US009445587B2

United States Patent
Ofek

(10) Patent No.: US 9,445,587 B2
(45) Date of Patent: Sep. 20, 2016

(54) PESTICIDE COMPOSITIONS AND PESTICIDAL PREPARATION

(71) Applicant: ECOLOGIC TECHNOLOGIES LTD., Luzit (IL)

(72) Inventor: Ido Ofek, Luzit (IL)

(73) Assignee: ECOLOGIC TECHNOLOGIES LTD., Luzit (IL)

( * ) Notice: Subject to any disclaimer, the term of this patent is extended or adjusted under 35 U.S.C. 154(b) by 0 days.

(21) Appl. No.: 14/186,716

(22) Filed: Feb. 21, 2014

(65) Prior Publication Data

US 2014/0170200 A1  Jun. 19, 2014

Related U.S. Application Data

(63) Continuation of application No. PCT/IL2012/050324, filed on Aug. 23, 2012.

(60) Provisional application No. 61/526,317, filed on Aug. 23, 2011.

(51) Int. Cl.
| | |
|---|---|
| *A01N 25/18* | (2006.01) |
| *A01N 25/00* | (2006.01) |
| *A01N 59/00* | (2006.01) |
| *A01N 59/04* | (2006.01) |
| *A01N 25/20* | (2006.01) |
| *A01N 59/06* | (2006.01) |
| *A01N 59/14* | (2006.01) |

(52) U.S. Cl.
CPC ............. *A01N 25/18* (2013.01); *A01N 25/00* (2013.01); *A01N 25/20* (2013.01); *A01N 59/00* (2013.01); *A01N 59/04* (2013.01); *A01N 59/06* (2013.01); *A01N 59/14* (2013.01)

(58) Field of Classification Search
CPC ...... A01N 25/00; A01N 59/00; A01N 59/04; A01N 59/14; A01N 2300/00; A01N 25/12; A01N 25/26; A01N 25/18; A01N 25/20; A01N 59/06; A01N 25/28
See application file for complete search history.

(56) References Cited

U.S. PATENT DOCUMENTS

| | | | | |
|---|---|---|---|---|
| 4,198,782 | A | * | 4/1980 | Kydonieus et al. ....... 47/58.1 R |
| 5,372,989 | A | * | 12/1994 | Geigle et al. ............. 504/367 |

FOREIGN PATENT DOCUMENTS

| | | |
|---|---|---|
| DE | 3439452 A1 | 5/1986 |
| DE | 3712487 A1 | 8/1988 |
| DE | 20100438 U1 | 3/2001 |
| EP | 0462347 A1 | 12/1991 |
| EP | 1811008 A2 | 7/2007 |
| WO | 2011/100297 A2 | 8/2011 |

OTHER PUBLICATIONS

Walker, Denise. Acids and Alkalis. 2007. Evans Brothers. p. 44.*
International Search Report of Appln. No. PCT/IL2012/050324 mailed Mar. 12, 2013.

(Continued)

*Primary Examiner* — Carlos Azpuru
*Assistant Examiner* — Casey Hagopian
(74) *Attorney, Agent, or Firm* — Browdy and Neimark, PLLC

(57) ABSTRACT

Disclosed is pesticidal particulate composition of matter, the particles comprising active substances, which react upon contact inside a pest body, the reaction generating a gaseous product and/or heat which destroy the pest. Pesticidal preparations, methods and kits are also disclosed.

15 Claims, 6 Drawing Sheets

(56) References Cited

OTHER PUBLICATIONS

Figure 1:
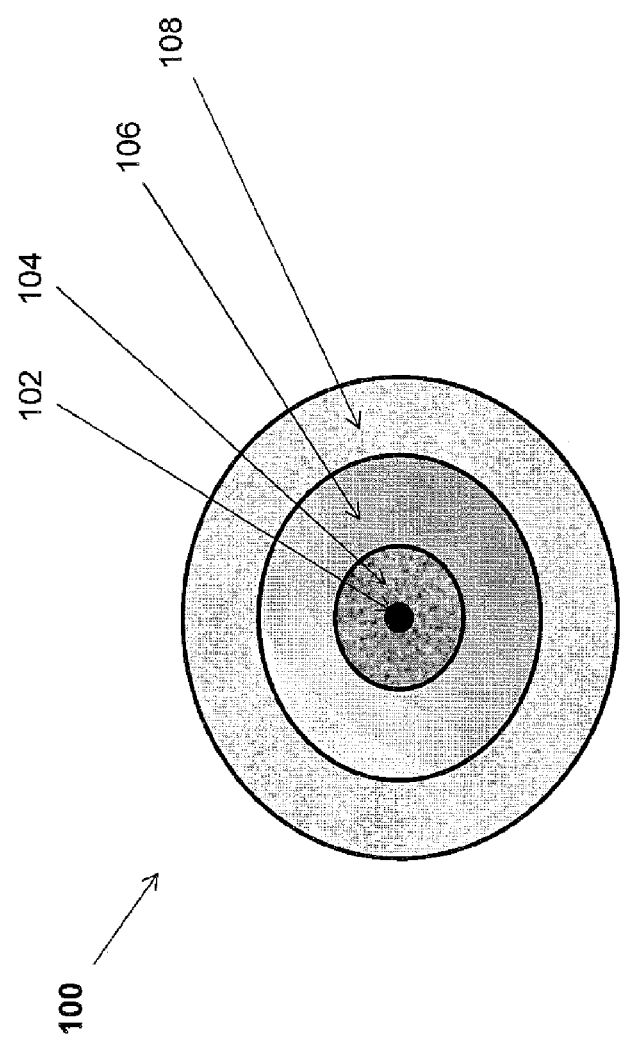

"Grade 10 Physical Sciences; Reactions in aqueous solution; Other types of reactions," Everything Maths and Science, Siyavula Technology-Powered Learning, downloaded in 2016, available at http://www.everythingmaths.co.za/science/grade-10/18-reactions-in-aqueous-solution/18-reactions-in-aqueous-solution-05.cnxmlplus.

"Typical Reactions Involving Acids," Chemistry for Physical Sciences, Launceston College, Tasmania Australia, downloaded in 2016, which can be found at: http://www.launc.tased.edu.au/online/sciences/PhysSci/pschem/acidbase/acidRxns.htm.

Silberberg, "Chemistry: The Molecular Nature of Matter and Change," Fourth Edition, McGraw-Hill Companies, New York, pp. 149 and 163 (2006).

"Natural Acids of Fruits and Vegetables," downloaded in 2016, found at http://www.hawkinswatts.com/documents/Natural%20Acids%20of%20Fruits%20and%20Vegetables.pdf.

"Acid-Base Reactions (Gas Producing)" LHS AP Chemistry, downloaded in 2016, which can be found at: https://sites.google.com/a/wrps.net/lhs-ap-chemistry/ap-chemistry-weblinks/strategies-for-writing-equations/acid-base-reactions.

"Sodium Carboxymethyl Cellulose—Supplier Data by Wolff Cellulosics a Division of Bayer Materialscience" Bayer Material Science, http://www.azom.com/article.aspx?ArticleID=2788; Date added: Apr. 5, 2005; Updated: Jul. 12, 2013.

* cited by examiner

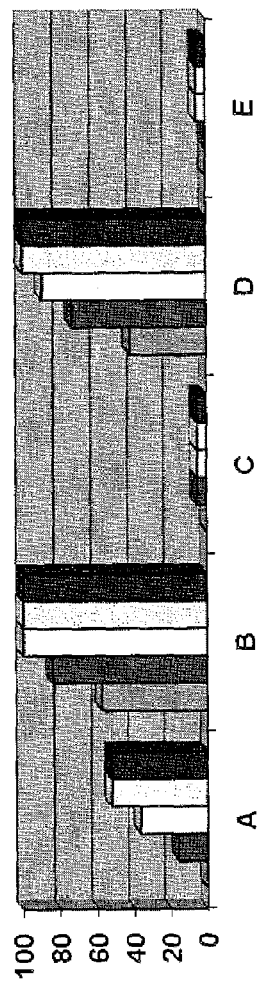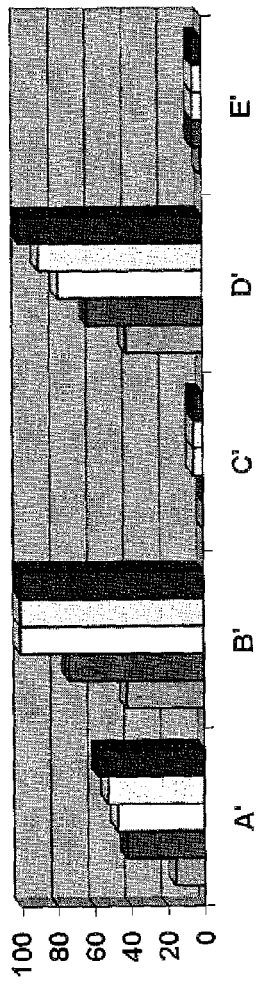
Figure 6A
Figure 6B

PESTICIDE COMPOSITIONS AND PESTICIDAL PREPARATION

FIELD OF THE INVENTION

This invention relates to pesticidal compositions and preparations.

BACKGROUND OF THE INVENTION

Insect resistance to toxic pesticides leads to major sanitary and economic problems in many sectors of society. Current approaches solving the problem based on existing technologies usually involve increasing the quantities of the applied pesticides, increasing the frequency of pesticides application and exploiting more powerful and lethal poisons. Solutions based on such approaches have several disadvantages, inter-alia because they only provide short-term solutions to the problem, as the pests eventually develop resistance to pesticides resulting in emergence of resistant strains and populations which can withstand high levels of pesticides as well as new chemical agents. Furthermore, the use of stronger pesticides, at increased frequency, also increases environmental damage associated therewith and has severe public health implications. In addition, pesticides are quite often poisonous and dangerous to non-pest species, which may be accidentally poisoned.

To control the population of pests a combination of various methods is usually practiced e.g., spraying pests and loci with pesticides, application of toxic baits, use of glue traps to physically trap the pests and thorough cleaning with detergents, which are known to cause environmental damage, in order to maintain hygienic conditions. Significant improvement of the efficacy of pest control and means for pest eradication are still necessary.

SUMMARY OF THE INVENTION

Based on a novel approach, the present inventor developed advanced pesticidal composition of matter, which controls pests by a chemical reaction initiated and occurring inside the pest body, which results with physical damage that may lead to death and destruction of the pests. The chemical reaction involves generation and evolution of gas bubbles such as $CO_2$ bubbles and might be accompanied with heat formation. The gas bubbles are trapped inside the insect body for example in the digestive system and/or respiratory system of said insect and that may cause, inter alia, suffocation and/or physical "explosion" of the insect. The entrapment of the formed gas bubbles may be achieved by aid of agents such as foaming, swelling or sticking agents comprised within the composition of matter of the invention. At times, the chemical reaction inside the pest body involves only generation of heat without gas formation. The heat evolved in the reaction may cause irreversible damage to various internal systems and organs inside the pest body e.g., the respiratory and digestion system. When heat formation is involved (with or without gas formation), the heat might cause burns in the internal systems of the pest which may result with dysfunction of essential systems and functions, eventually leading to death of the pest. For example, the heat may cause burns in the respiratory system which cause formation of holes in the pest's trachea that may result with failure of the respiratory system and suffocation of the pest.

The composition of matter according to the invention is highly effective against a wide range of pests, and is capable of eradicating the majority of the pests treated therewith, in terms of both variety of species and numbers, at a relatively short time frame e.g., few hours and at times within less than one hour after application e.g., after half an hour or after abut few minutes. Further, the efficacy of the compositions of the invention in terms of time frame is substantially as the chemical reaction inside the pest body occurs right after the consumption of the composition by the pest, thus, the effect of the reaction which occurs inside the pest body might be immediate.

The composition of matter according to the invention is stable for relatively long storage duration e.g., for at least months and/or years. Further, the composition comprises bait ingredients which are capable of attracting the pests for a relatively long period of time after the composition is applied to pests infected locations. Furthermore, the mechanism of action of the pesticidal composition of matter according to the present invention does not allow for the pest to develop resistance as in the case with many other pesticides which attack the nerve or neural system of the pest. Thus, the composition provides the advantage of long term efficacy.

The composition of matter according to the invention exhibits relatively low toxicity, if any, to creatures other than pests e.g., humans, pets, domestic animals and birds and the like, particularly in view of the different breathing and digestion systems, and considering the relatively low amounts of active ingredients comprised therein, which are per se non-toxic. The composition is relatively inexpensive to manufacture and may also provide "green" solutions to the environmental and ecological problems associated with the control of pests.

Thus, the present invention provides, in accordance with a first of its aspects, a pesticidal particulate composition of matter comprising particles, the particles comprising a first active substance and a second active substance, wherein contact between the first and second active substances inside a pest body leads to:
  (1) a reaction that generates at least one gaseous product, with or without heat generation; and/or
  (2) an exothermic reaction generating heat;
  wherein said at least one gaseous product and/or heat are capable of destroying the pest.

In a further aspect the present invention provides a pesticidal particulate composition of matter comprising particles, the particles comprising a core of an admixture of a first functional substance, a second functional substance, at least one inert additive and optionally at least one relaxant agent, wherein contact between the first and second active substances inside a pest body leads to:
  (1) a reaction that generates at least one gaseous product, with or without heat generation; and/or
  (2) an exothermic reaction generating heat;
  wherein said at least one gaseous product and/or heat are capable of destroying the pest.

In yet a further aspect, the present invention provides a pesticidal particulate composition of matter comprising a first active substance, a second active substance and at least one inert additive, wherein the reaction between the first and second active substances upon contact inside a pest body (e.g., in the aqueous environment therein), generates heat, the heat being capable of destroying the pest.

Yet, in a further aspect, the present invention provides a pesticidal particulate composition of matter comprising a first active substance, a second active substance, at least one inert additive and optionally at least one relaxant agent, wherein the reaction between the first and second active substances upon contact inside a pest body (e.g., in the aqueous environment therein), generates heat, the heat being capable of destroying the pest.

In yet a further aspect, the present invention provides a pesticidal particulate composition of matter comprising an individually coated first active substance and an individually coated second active substance, wherein the reaction between the first and second active substances upon contact with each other within a pest body generates heat, the heat being capable of destroying the pest.

In a further aspect, the present invention provides a pesticidal particulate composition of matter comprising an individually coated first active substance and an individually coated second active substance, wherein the first and second active substances form a gaseous product upon contact with each other within a pest body, the gaseous product being capable of destroying the pest.

In a further aspect, the present invention provides a pesticidal composition of matter comprising a mixture of particles of a first type and particles of a second type, each particle comprising a core of an active substance, individually coated at least in part with a first coating layer, wherein
- the core of the first type particles comprises a first functional substance and the core of the second type particles comprises a second functional substance, the first and second functional substances forming a gaseous product upon contact with each other (e.g., in aqueous environment inside a pest body), wherein optionally at least part of the gaseous product is in the form of gas bubbles;
- wherein the first coating layer comprises at least one material which prevents contact between the first and the second functional substance, which material disintegrates at least in part in a substantially aqueous environment to thereby enable contact between the first functional substance and the second functional substance, wherein the material in the first coating layer of the first type particles and in the first coating layer of the second type particles may be the same or different; and
- wherein optionally at least one of the first type particles and the second type particles further comprises a second coating layer which may be superimposed on the first coating layer, wherein the second layer comprises a material which prevents coalescence of gas bubbles optionally formed by the contact between the first functional substance and the second functional substance, wherein the material in the second coating layer of the first type particles and in the second coating layer of the second type particles may be the same or different.

In yet a further aspect, the present invention provides a pesticidal particulate composition of matter comprising a first functional substance and a second functional substance, wherein the first and second functional substances are each individually coated at least in part with a first coating layer;
- wherein the first and second functional substances form a gaseous product upon contact with each other (e.g., in an aqueous environment inside a pest body), wherein optionally at least part of the gaseous product is in the form of gas bubbles;
- wherein the first coating layer comprises at least one material which prevents contact between the first and the second functional substance, which material disintegrates at least in part in a substantially aqueous environment thereby enabling contact between the first functional substance and the second functional substance, wherein the material in the first coating layer of the first active substance and in the first coating layer of the second active substance may be the same or different;
- wherein at least one of the first functional substance and the second functional substance is optionally further coated at least in part with same or different second coating layer wherein the second coating layer comprises a material which prevents coalescence of gas bubbles optionally formed by the contact between the first functional substance and the second functional substance, wherein the said material in the second coating layer of the first functional substance and the said material in the second coating layer of the second functional substance may be the same or different; and
- wherein the first and second active substances are both comprised in a single particle.

In a further aspect, the present invention provides a pesticidal composition of matter comprising a mixture of particles of a first type and particles of a second type, each particle comprising a core of an active substance, individually coated at least in part with a first coating layer, wherein
- the core of the first type particles comprises a first functional substance and the core of the second type particles comprises a second functional substance, the reaction between the first and second functional substances upon contact with each other (e.g., in aqueous environment inside a pest body) generating heat;
- wherein the first coating layer comprises at least one material which prevents contact between the first and the second functional substance, which material disintegrates at least in part in a substantially aqueous environment to thereby enable contact between the first functional substance and the second functional substance, wherein the material in the first coating layer of the first type particles and in the first coating layer of the second type particles may be the same or different; and
- wherein optionally at least one of the first type particles and the second type particles further comprises a further coating layer which may be superimposed on the first coating layer.

In yet a further aspect, the present invention provides a pesticidal particulate composition of matter comprising a first functional substance and a second functional substance, wherein the first and second functional substances are each individually coated at least in part with a first coating layer;
- wherein the reaction between the first and second functional substances upon contact with each other (e.g., in an aqueous environment inside a pest body) generates heat;
- wherein the first coating layer comprises at least one material which prevents contact between the first and the second functional substance, which material disintegrates at least in part in a substantially aqueous environment thereby enabling contact between the first functional substance and the second functional substance, wherein the material in the first coating layer of the first active substance and in the first coating layer of the second active substance may be the same or different;
- wherein at least one of the first functional substance and the second functional substance is optionally further coated at least in part with same or different further coating layer; and
- wherein the first and second active substances are both comprised in a single particle.

In a further aspect, the present invention provides a pesticidal particulate composition of matter comprising a first active substance, a second active substance and at least one inert additive, wherein inside a pest body (e.g., in the aqueous environment therein) the first and second active substances form a gaseous product, the gaseous product being capable of destroying the pest.

In a further aspect, the present invention provides a pesticidal particulate composition of matter comprising a first active substance, a second active substance, at least one inert additive and optionally at least one relaxant agent, wherein inside a pest body (e.g., in the aqueous environment therein) the first and second active substances form a gaseous product, the gaseous product being capable of destroying the pest.

In yet a further aspect, the present invention provides a particulate composition of matter comprising particles, each particle comprising a core of an admixture of a first functional substance, a second functional substance, at least one inert additive and optionally at least one relaxant agent, wherein each said core is coated at least in part with a first coating layer;

wherein said first and second functional substances form a gaseous product in the aqueous environment inside a pest body, wherein optionally at least part of the gaseous product is in the form of gas bubbles;

wherein the first coating layer comprises at least one material which disintegrates at least in part in a substantially aqueous environment to thereby enable exposure of the first functional substance and the second functional substance to the aqueous environment inside a pest body;

wherein each of said particle is optionally further coated at least in part with a second coating layer wherein the second coating layer comprises a material which prevents coalescence of gas bubbles optionally formed at least in part by the first functional substance and the second functional substance.

In yet a further aspect, the present invention provides a particulate composition of matter comprising particles, each particle comprising a core of an admixture of a first functional substance, a second functional substance, at least one inert additive and optionally at least one relaxant agent, wherein each said core is coated at least in part with a first coating layer;

wherein the reaction between said first and second functional substances in the aqueous environment inside a pest body generates heat;

wherein the first coating layer comprises at least one material which disintegrates at least in part in a substantially aqueous environment to thereby enable exposure of the first functional substance and the second functional substance to the aqueous environment inside a pest body;

wherein each of said particle is optionally further coated at least in part with a further coating layer.

In another aspect, the present invention provides the composition according to the invention for use as a pesticide.

In a further aspect, the present invention provides a pesticidal preparation comprising a composition of matter according to the invention.

In yet a further aspect, the present invention provides a method of controlling pests wherein the method comprises exposure of the pests to the composition of matter according to the invention or to the pesticidal preparation according to the invention.

In yet a further aspect, the present invention provides a kit for controlling pests, said kit comprising:

a) particles of a first active substance;

b) particles of a second active substance;

c) means for mixing the constituents defined in a) and b);

d) means for applying the mixed constituents of c) to a pest-infected environment; and e) instructions for use.

In yet a further aspect the present invention provides a kit comprising:

a) a composition of matter according to the invention;

b) means for applying the composition of a) to a pest-infected environment; and c) instructions for use.

BRIEF DESCRIPTION OF THE DRAWINGS

In order to understand the invention and to realize how it may be carried out in practice, embodiments will now be described, by way of non-limiting example only, with reference to the accompanying drawings, in which:

FIG. 1 provides schematic illustration of one particle comprised within the composition of matter according to one embodiment of the invention; the particle comprising a core of an active substance.

FIG. 2 provides schematic illustration of a particulate composition of matter according to one embodiment of the invention; the composition comprises first and second active substances, each individually contained within first and second type particles, respectively.

FIG. 3 provides schematic illustration of a particulate composition of matter according to one embodiment of the invention; the composition comprises first and second active substances, each individually contained within first and second type particles, respectively. In the figure only the second active substance is coated with a first coating layer.

FIG. 4 provides schematic illustration of a particulate composition of matter according to one embodiment of the invention; the composition comprises first and second active substances contained within the same particle.

FIG. 5 provides schematic illustration of a particulate composition of matter according to an embodiment of the invention wherein the particle comprises a core of an admixture of a first and second functional substances and at least one inert additive.

FIGS. 6A-6B provide a comparison of the activity against pests achieved by the use of the composition of matter according to the invention and another pesticide composition.

DETAILED DESCRIPTION OF EMBODIMENTS

The present invention provides a composition of matter with superior effectiveness against pests. Utilizing the composition of matter according to the invention against a wide variety of pests, specifically insect pests surprisingly resulted with eradication of the pests. The composition of matter of the invention is stable and its pesticidal activity is maintained over long periods of time, and a mechanism of action which prevents development of pest physiological resistance thereto, which mechanism can be generally described as inducing a chemical reaction inside the pest body, resulting, for example, with physical/mechanical damage thereto, which leads to death and extermination/eradication of the pests. Thus, the composition of matter according to the invention may be efficiently used to control pests.

As used herein, the term "control pests" or any lingual variation thereof refers to at least one of leading to or causing pests extermination, death, eradication, suppression, prevention, destruction, destroying, repelling, mitigation or the like.

As used herein, the term "pests" refers but is not limited to arthropod insects, selected for example from ants, cockroaches (e.g., German cockroaches), flies, for example tsetse flies, wasps, crickets, fleas, aphids, lice, bed bugs, mosquitoes, termites, silverfish, woodworm and wood ants, carpet beetles, clothes moths and ticks.

As used herein, the terms "pesticidal", "insecticidal" or any lingual variations thereof are interchangeable and refer to a substance used for controlling pests.

Thus, firstly, the present invention provides, a pesticidal particulate composition of matter comprising a first active substance and a second active substance, wherein contact between the first and second active substances inside a pest body leads to:
 (1) a reaction that generates at least one gaseous product, with or without heat generation; and/or
 (2) an exothermic reaction generating heat;
  wherein said at least one gaseous product and/or heat are capable of destroying the pest.

In a further aspect the present invention provides a pesticidal particulate composition of matter comprising particles, the particles comprising a core of an admixture of a first functional substance, a second functional substance, at least one inert additive and optionally at least one relaxant agent, wherein contact between the first and second active substances inside a pest body leads to:
 (1) a reaction that generates at least one gaseous product, with or without heat generation; and/or
 (2) an exothermic reaction generating heat;
  wherein said at least one gaseous product and/or heat are capable of destroying the pest.

In a further aspect, the present invention provides a pesticidal particulate composition of matter comprising an individually coated first active substance and an individually coated second active substance, wherein the reaction between the first and second active substances upon contact with each other within a pest body generates heat, the heat being capable of destroying the pest.

In yet a further aspect, the present invention provides a pesticidal particulate composition of matter comprising individually coated first active substance and individually coated second active substance, wherein the first and second active substances form a gaseous product upon contact with each other within a pest body, the gaseous product being capable of destroying the pest.

In some embodiments each of the first and second individually coated active substances is contained in first and second type particles, respectively.

In some further embodiments both of the individually coated first and second active substances are contained in a same particle.

In some embodiments, according to all aspects of the invention, each of the first and second active substances is contained in first and second type particles, respectively.

In some further embodiments, according to all aspect of the invention the first and second active substances are contained in a same particle.

In some embodiments, according to all aspects of the invention, the first active substance and the second active substance may each individually be coated at least in part with a first coating layer.

As used herein, the terms "first active substance", "first functional substance", "first active agent" and "first functional agent" or any lingual variations thereof are interchangeable.

As used herein, the terms "second active substance", "second functional substance", "second active agent" and "second functional agent" or any lingual variations thereof are interchangeable.

As used herein, the terms "coated", "covered", "wrapped" "surrounded with", "impregnated with" or any lingual variations thereof are interchangeable. In some embodiments the coating is 100%, i.e. covers the whole surface area of the particle, or core, or active substance, or a former layer, etc. In some other embodiments the coating is less than 100% e.g., 90%. 80%, 70%, 60%, 50%, 40%, 30%, 20%, 10% etc. of the surface area of the particle, or core, or active substance, or a former layer, etc. At times, coating of less than 100% is referred to as coated in part. In all aspects and embodiments in which particles are coated with more than one layer, for example, two three or even more coating layers, they may be referred to as multilayered particles. In all aspects and embodiments in which particles are coated with more than one layer, for example, two, three or even more coating layers, the particles may be referred to as "multilayered particles".

In some embodiments the coating of the active substances according to all aspects of the invention is aimed inter alia at protecting the first functional agent and the second functional agent from contact with each other. It is contemplated within the scope of the present invention that coating of either the first functional agent or the second functional agent may be sufficient to prevent contact between the first functional agent and the second functional agent. The coating of the active substances may also be aimed at, inter alia, protecting the first functional agent and/or the second functional agent from contact with their environment/vicinity/surroundings. Thus, the coating may further provide for stable storage conditions of the composition of matter according to the invention, rendering the composition stable for relatively long storage duration e.g., for at least months and/or years. It is further noted in this respect that the first and second active substances according to the invention may be comprised within a kit as will be described in more detail herein below. At times, in the kit according to the invention, the first and the second active substances may be separately packed and sealed so as to prevent contact between them and optionally to prevent their exposure to deteriorating or otherwise damaging conditions e.g., humidity, thus providing stable storage conditions for relatively long periods of time.

It is noted that at times coating of only one of the first or second active substances with a first coating layer may be sufficient inter alia for preventing the contact between the first and second active substances in the composition of matter according to the invention. To this end, the term "coated at least in part" with respect to the first coating layer is to be envisaged as only one of the active substances (first or second) is coated with the first coating layer. Thus, in some embodiments, according to all aspects of the invention, only the first active substance is coated with a first coating layer and the second active substance is only coated with the second coating layer described herein. In some further embodiments only the second active substance is coated with a first coating layer and the first active substance is only coated with the second coating layer which is described herein.

At times, individual coating of the first and second active substances in the composition of matter according to the present disclosure may not be necessary. To this end, the first and second active substances may, to some extent, already be in contact with each other prior to entering a pest body, however such contact does not result with gas forming reaction and/or heat formation. The gas production and/or heat formation occurs in the substantially aqueous environment inside the pest body.

In a further aspect, the present invention provides a pesticidal particulate composition of matter comprising a first active substance, a second active substance, at least one inert additive and optionally at least one relaxant agent, wherein the first and second active substances form a gaseous product inside a pest body (e.g., in the aqueous environment therein), the gaseous product being capable of destroying the pest.

In yet a further aspect, the present invention provides a pesticidal particulate composition of matter comprising a first active substance, a second active substance and at least one inert additive, wherein the first and second active substances form a gaseous product inside a pest body (e.g., in the aqueous environment therein), the gaseous product being capable of destroying the pest.

In a further aspect, the present invention provides a pesticidal particulate composition of matter comprising a first active substance, a second active substance and at least one inert additive, wherein the reaction between the first and second active substances upon contact inside a pest body (e.g., in the aqueous environment therein) generates heat, the heat being capable of destroying the pest.

Yet, in a further aspect, the present invention provides a pesticidal particulate composition of matter comprising a first active substance, a second active substance, at least one inert additive and optionally at least one relaxant agent, wherein the reaction between the first and second active substances upon contact inside a pest body (e.g., in the aqueous environment therein) generates heat, the heat being capable of destroying the pest.

In some embodiments, according to all aspects of the invention, the first functional substance, the second functional substance and the at least one inert additive are comprised within a core. In some further embodiments the core comprises an admixture of the first functional substance, the second functional substance and the at least one inert additive. At times the core may further comprise a relaxant agent described herein.

As used herein the term "admixture" refers to a physical combination of two or more substances e.g., a mixture of a first and second active substances, in which the identities of the substances are retained.

In some embodiments, according to all aspects of the invention, the composition of the invention e.g., at least one particle comprised therein and/or the core comprised therein and/or a first active substance comprised therein and/or a second active substance comprised there may be coated at least in part with a first coating layer. The first coating layer may be further coated at least in part with a second coating layer described herein and/or a third coating layer described herein and/or a further coating layer described herein.

As used herein, the term "inert additive" refers to an inactive material which serves as a carrier or a binder. The inert additive may stabilize the structure of the composition according to the invention (e.g., the active substances comprised therein, the core of the composition) inter alia preventing reaction between the first and second active substances prior to being consumed by the pest. The inert additive may also provide protection of the active substances by isolating them from their environment, thus ensuring stable storage conditions of the composition of matter according to the invention, as well as preventing the exposure of the active substances to damaging conditions such as humidity. The inert additive may be but is not limited to $CaSO_4$ and/or $CaO$. In some embodiments the inert additive is $CaSO_4$.

As used herein, the terms "relaxant agent" or any lingual variation thereof refers to a material which serves as a muscle relaxant. Without wishing to be bound by any theory, the relaxant material may lead to relaxation of the pest e.g., reducing the tendency of pests to run around, which may result with presence of the pest in the location of the pesticidal composition for a longer period of time, this may lead to consumption of higher amounts of the pesticidal composition which may increase the efficacy thereof. Furthermore and without being bound thereto, the relaxant material may cause relaxation of the muscles of the pest e.g., the respiratory muscles, which may result with enlargement of the pest's trachea, this may enable entry of higher amounts of the composition of matter to the respiratory system which may result with a more efficient suffocation of the pest leading to the destruction thereof. Thus, the relaxant agent may provide the pesticidal composition of matter of the invention with a synergistic destruction effect of the pest. The relaxant agent may be but is not limited to KBr, NaBr or any combinations of the same. In some embodiments the relaxant agent may be at least one anticonvulsant. In some further embodiments the relaxant agent may be an anthelmintic material, for example Ivermectin.

In some embodiments the relaxant agent is KBr.

In some embodiments, according to all aspects of the invention, the composition of matter of the invention may optionally comprise a relaxant agent. The relaxant agent may be comprised within the core of the composition, within a particle of the composition or within any or at least one of the first, second or third coating layer detailed herein.

In some embodiments the contact between the first functional substance/agent and the second functional substance/agent according to all aspects of the invention may be a chemical interaction and/or a physical contact accompanied by a chemical interaction/reaction which leads to the formation of gas. The evolution of gas may be a result of the interactions between the first and the second functional substances as well as with any other material comprised within the environment surrounding the first and the second functional substances e.g., water molecules.

In some embodiments according to all aspects of the invention, the first active substance may be, but is not limited to boric acid ($H_3BO_3$), metaboric acid ($HBO_2$), formic acid ($HCO_2H$), citric acid and glycerin. Mixtures of these agents are also contemplated within the scope of the invention. In a specific embodiment according to all aspects of the invention the first active substance is boric acid. In a further specific embodiment according to all aspects of the invention the first active substance is metaboric acid.

In some further embodiments according to all aspects of the invention the second active substance may be, but is not limited to sodium bicarbonate ($NaHCO_3$), calcium carbonate ($CaCO_3$) and potassium permanganate ($KMnO_4$). Mixtures of these agents are also contemplated within the scope of the invention. In a specific embodiment according to all aspects of the invention the second active substance is sodium bicarbonate.

In some further embodiments according to all aspects of the invention the second active substance may be an oxidizing agent such as but not limited to $KMnO_4$.

In yet further embodiments according to all aspects of the invention the first active substance may be an acidic substance such as, but not limited to boric acid, metaboric acid, formic acid, and citric acid. The acidic substance may be a strong, weak or mild acid. The acid may be an organic acid such as citric acid. In some embodiments the acidic substance is $H_3BO_3$. In other embodiments the acidic substance is $HBO_2$. At times the acid may be a water-soluble acid e.g., citric acid. At time the acid may be a water-insoluble acid e.g., boric acid and metaboric acid.

In some embodiments according to all aspects of the invention the second active substance may be a basic substance. The basic substance may be a strong, weak or mild base. In some embodiments the basic substance is $NaHCO_3$.

In some embodiments according to all aspects of the invention the first active substance may be an acidic substance and the second active substance may be a basic substance.

In some embodiments according to all aspects of the invention the first active substance and the second active substance may each individually be present in the composition of matter according to the invention in their solid form.

In a specific embodiment according to all aspects of the invention the acidic substance may be $H_3BO_3$ and the basic substance may be $NaHCO_3$ which upon contact (interaction) in a substantially aqueous environment e.g., upon introduction to the pest's body, form gaseous $CO_2$ according to the following suggested reaction:

$$NaHCO_{3(s)} + H_3BO_{3(s)} \leftrightarrows CO_{2(g)} + Na^+ + H_2BO_3^- + H_2O_{(l)}$$

It is noted that at times the reaction between the first active agent e.g., $H_3BO_3$ and the second active agent e.g., $NaHCO_3$ might reach to completion (completed reaction). In some embodiments the said reaction might not reach to completion thus the reaction might be a partial reaction (e.g., a partial acid-base reaction).

In a specific embodiment according to all aspects of the invention the first substance may be $H_3BO_3$ and the second substance may be $CaCO_3$ which upon contact (interaction) in a substantially aqueous environment e.g., upon introduction to the pest's body, form gaseous $CO_2$.

In a specific embodiment according to all aspects of the invention the acidic substance may be $HBO_2$ and the basic substance may be $NaHCO_3$ which upon contact (interaction) in a substantially aqueous environment e.g., upon introduction to the pest's body, form gaseous $CO_2$ according to the following suggested reaction:

$$NaHCO_{3(s)} + HBO_{2(s)} \leftrightarrows CO_{2(g)} + Na^+ + H_2BO_3^-$$

It is noted that at times the reaction between the first active agent e.g., $HBO_2$ and the second active agent e.g., $NaHCO_3$ might reach to completion (completed reaction). In some embodiments the said reaction might not reach to completion thus the reaction might be a partial reaction (e.g., a partial acid-base reaction). Thus, in a specific embodiment according to all aspects of the invention the acidic substance may be $HBO_2$ and the basic substance may be $NaHCO_3$.

In a specific embodiment the composition acidic substance is $HBO_2$, the basic substance is $NaHCO_3$ and the inert additive is a combination of $CaSO_4$ and $KBr$.

In a specific embodiment according to all aspects of the invention the first substance may be $HBO_2$ and the second substance may be $CaCO_3$ which upon contact (interaction) in a substantially aqueous environment e.g., upon introduction to the pest's body, form gaseous $CO_2$.

In yet a further specific embodiment according to all aspects of the invention the first substance may be glycerin (glycerol) and the second substance may be potassium permanganate which exothermally interact upon contact with each other (e.g., in a substantially aqueous environment, upon entering the pest's body), and produce $CO_2$ as one of the reaction products.

In a further aspect of the invention, it is contemplated that any first and second active substances that upon contact with each other optionally in the presence of water may undergo an exothermic reaction may be practiced in the present invention. Without being bound by any theory, it is proposed that the heat emitted during the exothermic reaction may lead to the destruction of the pest.

In yet a further embodiment according to all aspects of the invention, the composition of matter comprises a first active substance (e.g., an acid) and second active substance (e.g., a base) which upon contact with each other inside the pest body lead to a reaction which forms a gaseous product (with or without heat formation), the composition further comprising an intermediate layer, wherein said intermediate layer comprises a further first active substance (e.g., glycerol) and a further second active substance (e.g., potassium permanganate) wherein the further first active substance and the second active substance lead to an exothermic reaction upon contact with each other (e.g., in the substantially aqueous environment inside the pest's body). The intermediate coating layer covers at least in part the first and/or second active substances per-se or comprised within a core or within a particle. The intermediate coating layer may be further coated with a first coating layer described herein, the first coating layer may be coated with a second coating layer described herein or with a third coating layer described herein, and the second coating layer may be coated with a third coating layer described herein.

In some embodiments the first active substance and the second active substance are present in the composition of matter according to all aspects of the invention at ratios which are in accordance with the stoichiometry of the reaction between them. For example, for the reaction between sodium bicarbonate and boric acid described above, the ratio between the first and second active substance may be an equimolar ratio (1:1 molar ratio). In case of different stoichiometry of the reaction between the two (or more) active substances, their ratio in the composition of matter of the invention can be determined based on the stoichiometry of the reaction, where one or the other substances may be present in excess molarity, as long as such excess does not adversely affect the reaction between the active substances to produce the gaseous product, in the above reaction carbon dioxide.

In a specific embodiment the $H_3BO_3$ acidic agent and the $NaHCO_3$ basic substance are present in the composition of matter according to all aspects of the invention at an equimolar ratio.

In a specific embodiment the $HBO_2$ acidic agent and the $NaHCO_3$ basic substance are present in the composition of matter according to all aspects of the invention at an equimolar ratio.

Without being bound by theory, the reactants/products resulting from the reaction between the first and the second active agents may be of substantially natural pH (about 7.0), not affecting the pH of the environment within the body of the pest (e.g., insect) by acidity and/or alkalinity.

In some embodiments according to all aspects of the invention the first coating layer may comprise at least one material/substance which prevents contact between the first active substance and the second active substance and/or which prevents contact between the active substances (first and/or second) themselves and with their surroundings, which material/substance disintegrates at least in part in a substantially aqueous e.g., within the pest body, to thereby enable contact between the first active substance and the second active substance and/or exposure of the first and second active substances to the aqueous environment within the pest body. In some embodiments the material in the first coating layer of the first active substance and in the first coating layer of the second active substance may be the same or different.

As used herein the terms “disintegrate”, “dissolve”, “break down”, “degrade” or any lingual variations thereof are interchangeable. It is noted that disintegration of material in the first layer of the composition of matter according to the invention may be mechanical/physical disintegration or may occur due to exposure of the particles of the invention to a substantially aqueous environment e.g., in the pest body and/or to exposure thereof to protease activity which may result in a proteolytic degradation of any proteinous material in the composition of the invention, or other enzymes that can enzymatically degrade any materials comprised in the composition of the invention as coating material, additives, etc. As a result of the disintegration the first and second active substances may be exposed to the surrounding and come into contact with each other to thereby produce gaseous product/s. It is noted that the term disintegration is not limited to the disintegration of the material in the first coating layer only. As detailed herein, each of the first and second active substances may be further coated with additional layers, for example a second and/or third coating layers. Thus, it is envisaged that the term disintegration may also refer to the disintegration of at least one of the coating layers which coat the first and/or the second active substances comprised within the composition of matter according to the invention.

As used herein, the term “substantially aqueous environment” refers to an environment comprising water. Without being limited thereto, the environment may be one of a water solution, an aqueous buffer solution, water-in-oil or oil-in-water solutions and the like. The substantially aqueous environment may be a physiological fluid or environment, such as, but not limited to gastric juices, blood, lymph and other bodily fluids, or a physiological internal bodily environment, such as the environment inside a pest body, or any internal tissues or organs inside the pest body. At time the term “environment” is interchangeable with the term “surrounding” or “surroundings”.

In some embodiments according to all aspects of the invention the material in the first coating layer which prevents contact between the first active substance and the second active substance and/or which prevents contact between the first and second active substances and their surroundings may be selected from the group consisting of proteins, carbohydrates, nutrients, synthetic materials and any combination of the same. In some embodiments the material is a hygroscopic material. At times, the hygroscopic material may be rice starch.

In some embodiments according to all aspects of the invention the protein may be selected from the group consisting of dairy proteins, meat proteins, egg proteins, plant proteins and any combination of the same. At times the protein is a whey protein.

In a specific embodiment according to all aspects of the invention the first coating layer may comprise at least a whey protein, and optionally rice starch.

It is noted that the protein comprised within the first coating layer of the composition of matter according to the invention may vary depending on the pest to be controlled.

In some embodiments at least one of the first active substance and the second active substance may be further coated at least in part with a same or different second coating layer. It is noted in this respect and regarding to all aspects of the invention that when the first and second active substances are contained within individual particles e.g., a first and second type particle, respectively, the second coating layer of the first active substance and the second coating layer of the second active substance may be the same or different layer. It is further noted in this respect and regarding all aspects of the invention that when the first and second active substances are contained within the same particle they may be simultaneously coated at least in part with the same second coating layer.

In some embodiments according to all aspects of the invention the first and second coating layers may be superimposed. In some further embodiments the superimposed first and second coating layers may be mixed with each other at least in part e.g., 90%. 80%, 70%, 60%, 50%, 40%, 30%, 20%, 10% etc. Superimposed layers may be overlapping at least in part. In yet further embodiments the first and second coating layers may be partly superimposed e.g., wherein the peripheries of the first and the second coating layers not strictly superimposed.

In some embodiments the second coating layer may comprise at least one material selected from the group consisting of a foaming agent, a swelling agent, adhesive agent (e.g., a gum), anti-coalescence agent and any combination of the same.

In some embodiments according to all aspects of the invention the material in the second coating layer of the first active substance and in the second coating layer of the second active substance may be the same or different.

In some embodiments according to all aspects of the invention the foaming agent may be but is not limited to carboxymethyl cellulose (CMC).

In some embodiments according to all aspects of the invention the adhesive agent may be, but is not limited to, any one of xanthan gum and guar gum.

In a specific embodiment according to all aspects of the invention the second coating layer may comprise carboxymethyl CMC and xanthan gum.

In some embodiments, according to all aspects of the invention, at least one material selected from the group consisting of a foaming agent, a swelling agent, adhesive agent (e.g., a gum), anti-coalescence agent and any combination of at least two thereof may be comprised in the first coating layer of the composition according to the invention. At times, CMC may be present in the first coating layer of the composition according to the invention.

In some embodiments according to all aspects of the invention at least one of the first active substance and the second active substance may be further coated with a third coating layer, wherein the third coating layer may comprise at least one specific insect attractant which may assist in attracting the pests to the composition of matter according to the invention. It is noted that when the first and second active substances are contained within individual particles e.g., a first and second type particle, respectively, the third coating layer of the first active substance and the third coating layer of the second active substance may be the same or different layer. It is further noted that when the first and second active substances are contained within the same particle they may each be coated at least in part with the same third coating layer.

In some embodiments according to all aspects of the invention the first and/or second and/or third coating layers may be superimposed. In some further embodiments the first and/or second and/or third coating layers may be mixed with each other at least in part e.g., 90%. 80%, 70%, 60%, 50%, 40%, 30%, 20%, 10% etc.

In yet further embodiments according to all aspects of the invention the first and/or second and/or third coating layers may be partly superimposed e.g., wherein the edges of the coating layers (first, second and/or third) may not be strictly superimposed.

In some embodiments according to all aspects of the invention the specific insect attractant in the third coating layer of the at least one of the first active substance and the second active substance may be the same or different.

In some embodiments according to all aspects of the invention the insect attractant may be a pest/insect baiting agent, such as a flavoring agent. The flavoring agent may be a sugar e.g., glucose or cane sugar.

In some embodiments according to all aspects of the invention the pest/insect baiting agent may be a fragrance or a pheromone.

In some embodiments the composition of matter according to the invention may further comprises at least one additive.

In some embodiments according to all aspects of the invention the at least one additive may be selected from the group consisting of potato starch, sugar (e.g., powdered sugar), salt (e.g., sea salt), butyric acid and any combination of at least two of them.

In some embodiments according to all aspects of the invention the said at least one additive may be selected from the group consisting of potato starch, sugar (e.g., powdered sugar), salt (e.g., sea salt), crystal menthol and any combination of at least two of them.

In a specific embodiment according to all aspects of the invention the additive may be a combination of any at least two of potato starch, powdered sugar, NaCl, KCl and butyric acid.

In a specific embodiment according to all aspects of the invention the additive may be a combination of any at least two of potato starch, powdered sugar, NaCl, KCl and crystal menthol.

In a further aspect, the present invention provides a pesticidal composition of matter comprising a mixture of particles of a first type and particles of a second type, each particle comprising a core of an active substance, individually coated at least in part with a first coating layer, wherein
the core of the first type particles comprises a first functional substance and the core of the second type particles comprises a second functional substance, the first and second functional substances forming a gaseous product upon contact with each other e.g., in a substantially aqueous environment, wherein optionally at least part of the gaseous product is in the form of gas bubbles;
wherein the first coating layer comprises at least one material which prevents contact between the first and the second functional substance, which material disintegrates at least in part in a substantially aqueous environment to thereby enable contact between the first functional substance and the second functional substance, wherein the material in the first coating layer of the first type particles and in the first coating layer of the second type particles may be the same or different; and
wherein optionally at least one of the first type particles and the second type particles further comprise a second coating layer which may be superimposed with the first coating layer, wherein the second layer comprises a material which prevents coalescence of the gas bubbles optionally formed by the contact between the first functional substance and the second functional substance, wherein the material in the second coating layer of the first type particles and in the second coating layer of the second type particles may be the same or different.

In some embodiments at least one of the first type particles and the second type particles may further comprise a third coating layer which may be superimposed at least in part with at least one of the first and second coating layers, wherein the third coating layer may comprises at least one specific insect attractant, wherein the specific insect attractant in the third coating layer of the at least one of the first type particles and said second type particles may be the same or different.

In some embodiments the composition may further comprises at least one additive.

In some embodiments the material which prevents contact between the first and the second functional substance and/or which prevents contact between the first and second active substances and their surroundings prior to the introduction to the pest body and comprised in the first coating layer may be selected from the group consisting proteins, carbohydrates, nutrients, other animal-, insect-, plant- or microorganism-derived materials, synthetic materials and any combination of the same.

In some embodiments the protein may be selected from the group consisting of dairy proteins, meat proteins, egg proteins, plant proteins and any combination of the same. At times the protein is a whey protein.

In some embodiments the first layer optionally may further comprise at least one hygroscopic material. At times the hydroscopic material is rice starch.

In a specific embodiment the first layer may comprise at least one whey protein and optionally rice starch.

In some embodiments according to all aspects of the invention the second coating layer may comprise at least one material selected from the group consisting of a foaming agent, a swelling agent, adhesive agent (e.g., a gum), anti-coalescence agent and any combination of the same. The aforementioned material may stabilize the bubbles foam by preventing coalescence of the gas bubbles optionally formed by the contact between the first functional substance and the second functional substance. As used herein, preventing coalesces may be envisaged inter-alia as preventing rupture and/or breakdown of the gas bubbles. It is further noted in this respect that the gaseous product produced upon contact between the first and the second functional substance and/or upon exposure of the first and the second functional substance to the substantially aqueous environment in the pest body may be present at least in part is in the form of bubbles. Without wishing to be bound by any theory, the inventors of the present disclosure believe that the at least one material that prevents the coalescence of the gas bubbles may function as foaming and/or swelling agent that entraps the bubbles of the gaseous product produced upon contact of the first and the second functional substance and form a stable foam. The at least one material that prevents the coalescence of the gas bubbles may be an adhesive material (e.g., a gum)

that adhere to the insect body for example while foaming and/or swelling. It is believed that the entrapment and/or foaming and/or swelling and/or adherence may result with blockage of at least one of the pest's inner body parts e.g., part of the digestion system and/or part of the respiratory system (e.g., at least one tracheal in the pest's tracheal system). Thus, the at least one material that prevents the coalescence of the gas bubbles may assist in causing dysfunction of at least one essential system in the pest's body which may result for example with the death of the pest. The prevention of coalescence of gas bubbles may lead inter alia blockage of entry of air to the pest via the respiratory system and thus to suffocation of the pest.

In all aspects of the invention wherein contact between the first and second active substances inside the pest body leads to heat generation only (without gas production) the presence of at least one material in the second coating layer, the material is selected from the group consisting of a foaming agent, a swelling agent, adhesive agent, anti-coalescence agent and any combination of the same, might not be required. Thus, in such aspects the presence of the said at least one material is optional. To this end, according to all aspects of the invention wherein only heat generation is involved upon contact/interaction between the first and second active substances without gas production, the second layer disclosed herein might not be required and thus the first coating layer may be further coated directly with the third coating layer.

In some embodiments of the invention, specifically where the first and second active agents are each comprised in the particles of a first type and particles of a second type, respectively, the particles may be mixed at a ratio that provides a stoichiometric molar ratio between the first active substance and the second active substance in accordance with the stoichiometry of the chemical reaction between them upon contact. At times the particles of a first type and particles of a second type may be mixed to provide an equimolar ratio (1:1) between the first and the second active agents. In some embodiments, where the first and second active agents are both comprised in the same particle (either in the same core or in individual cores or in an inert agent-containing mixture according to the invention), the ratio between them may be, mutatis mutandis, in accordance with the stoichiometry of the reaction between them upon contact.

In a further aspect the present invention provides a pesticidal particulate composition of matter comprising a first functional substance and a second functional substance, wherein the first and second functional substances are each individually coated at least in part with a first coating layer;
  wherein the first and second functional substances form a gaseous product upon contact with each other, wherein optionally at least part of the gaseous product is in the form of gas bubbles;
  wherein the first coating layer comprises at least one material which prevents contact between the first and the second functional substance, which material disintegrates at least in part in a substantially aqueous environment thereby enabling contact between the first functional substance and the second functional substance, wherein the material in the first coating layer of the first active substance and in the first coating layer of the second active substance may be the same or different;
  wherein at least one of the first functional substance and the second functional substance is optionally further coated at least in part with same or different second coating layer wherein the second coating layer comprises a material which prevents coalescence of the gas bubbles optionally formed by the contact between the first functional substance and the second functional substance, wherein the material in the second coating layer of the first functional substance and in the second coating layer of the second functional substance may be the same or different; and
  wherein the first and second active substances are contained in a same particle.

In some embodiments at least one of the first functional substance and the second functional substance may be further coated with a same or different third coating layer wherein the third coating layer may comprise at least one specific insect attractant, wherein the specific insect attractant in the third coating layer of the at least one of the first functional substance and the second functional substance may be the same or different.

In some embodiments the composition may further comprise at least one additive.

In a further aspect, the present invention provides a pesticidal composition of matter comprising a mixture of particles of a first type and particles of a second type, each particle comprising a core of an active substance, individually coated at least in part with a first coating layer, wherein
  the core of the first type particles comprises a first functional substance and the core of the second type particles comprises a second functional substance, the reaction between the first and second functional substances upon contact with each other (e.g., in aqueous environment inside a pest body) generating heat;
  wherein the first coating layer comprises at least one material which prevents contact between the first and the second functional substance, which material disintegrates at least in part in a substantially aqueous environment to thereby enable contact between the first functional substance and the second functional substance, wherein the material in the first coating layer of the first type particles and in the first coating layer of the second type particles may be the same or different; and
  wherein optionally at least one of the first type particles and the second type particles further comprises a further coating layer which may be superimposed on the first coating layer.

In yet a further aspect, the present invention provides a pesticidal particulate composition of matter comprising a first functional substance and a second functional substance, wherein the first and second functional substances are each individually coated at least in part with a first coating layer;
  wherein the reaction between the first and second functional substances upon contact with each other (e.g., in an aqueous environment inside a pest body) generates heat;
  wherein the first coating layer comprises at least one material which prevents contact between the first and the second functional substance, which material disintegrates at least in part in a substantially aqueous environment thereby enabling contact between the first functional substance and the second functional substance, wherein the material in the first coating layer of the first active substance and in the first coating layer of the second active substance may be the same or different;

wherein at least one of the first functional substance and the second functional substance is optionally further coated at least in part with same or different further coating layer; and wherein the first and second active substances are both comprised in a single particle.

It is noted that the aforementioned further coating layer is similar to the third coating layer disclosed herein, thus, all embodiments detailed herein in connection with the third coating later are applicable to the aforementioned further coating layer.

In yet a further aspect, the present invention provides a particulate composition of matter comprising particles, each particle comprising a core of an admixture of a first functional substance, second functional substance, at least one inert additive and optionally at least one relaxant agent, wherein each said core is coated at least in part with a first coating layer;

wherein said first and second functional substances form a gaseous product in the aqueous environment inside a pest body, wherein optionally at least part of the gaseous product is in the form of gas bubbles;

wherein the first coating layer comprises at least one material which disintegrates at least in part in a substantially aqueous environment to thereby enable exposure of the first functional substance and the second functional substance to the aqueous environment inside a pest body;

wherein each of said particle is optionally further coated at least in part with a second coating layer wherein the second coating layer comprises a material which prevents coalescence of the gas bubbles optionally formed at least in part by the first functional substance and the second functional substance.

In yet a further aspect, the present invention provides a particulate composition of matter comprising particles, each particle comprising a core of an admixture of a first functional substance, a second functional substance, at least one inert additive and optionally at least one relaxant agent, wherein each said core is coated at least in part with a first coating layer;

wherein the reaction between said first and second functional substances in the aqueous environment inside a pest body generates heat;

wherein the first coating layer comprises at least one material which disintegrates at least in part in a substantially aqueous environment to thereby enable exposure of the first functional substance and the second functional substance to the aqueous environment inside a pest body;

wherein each of said particle is optionally further coated at least in part with a further coating layer.

It is noted that the aforementioned further coating layer is similar to the third coating layer disclosed herein, thus, all embodiments detailed herein in connection with the third coating later are applicable to the aforementioned further coating layer.

In some embodiments the substances comprised in the composition of matter according to all aspects of the invention (e.g., first and/or second active substances and/or any substance comprised in the first and/or second and/or third coating layer according to the invention) may be in the form of aggregates.

In some embodiments the core of the admixture of the first and second functional substances, the at least one inert additive and the optionally at least one relaxant agent may be further coated with a third coating layer wherein the third coating layer may comprise at least one specific insect attractant.

In some embodiments according to all aspects of the invention the third coating layer may comprise animal-, insect-, plant- or microorganism-derived materials. Non limiting examples are to bone powder, powdered bones, fish powder, milk powder, peanut powder, vegetable powder and dead yeast powder.

It is noted that the insect attractants comprised within the third coating layer of the composition of matter according to all aspects of the invention may vary depending on the pest to be controlled. For example; the third layer may comprise wood powder starch when controlling termites is of interest; the third layer may comprise at least one of dry bone powder, peanut powder, milk powder and vegetable powder containing vegetarian protein and starch when controlling ants is of interest; the third layer may comprise lactic acid when controlling bed bugs is of interest; the third layer may comprise at least one of dead yeast powder, fish powder and bone powder when controlling flies is of interest; the third layer may comprise powdered bones when controlling fleas or flea larvae is of interest.

In some embodiments the composition may further comprise at least one additive.

In some embodiment the composition according to the invention is provided in the form of a powder.

The size of the particles in the particulate composition of matter according to the invention may vary for example from 0.01 mm to 0.1 mm. The size may also be indicated by passing through for example a Mesh of 2540-254.

In a further aspect the present invention provides a composition of matter according to the invention for use as a pesticide.

In a yet further aspect the present invention provides a pesticidal preparation comprising a composition of matter according to the invention optionally further comprising at least one of additives, excipients, diluents and carriers.

In some embodiments the preparation may be an insecticidal, miticidal or acaricidal preparation.

In yet a further aspect the present invention provides a method of controlling at least one pest wherein the method comprises exposure of the at least one pest to the composition of matter according to the invention or to the pesticidal preparation according to the invention. The exposure may be envisaged as having the composition of matter available to the pest e.g., by means of spreading, spraying, aerosol spraying, placing, powdering and the like of the composition of matter in the environment available to the pest. In some embodiments application of the composition of matter of the invention may be aerial application, for example, when pest control is of interest in areas with crops such as plantations.

In yet a further aspect the present invention provides a kit comprising:

a) particles of a first active substance;
b) particles of a second active substance;
c) means for mixing the constituents defined in a), b);
d) means for applying the mixed constituents of c) to a pest-infested environment; and
e) instructions for use.

In the aforementioned kit according to the invention the first and the second active substances are separately packed and sealed so as to prevent the contact thereof and optionally to prevent their exposure thereof to the surroundings e.g., humidity. The kit may comprise means for admixing the first and the second active substances as well as means for applying the active substances for example to the infested area of interest, for example by aerosol.

Alternatively, the kit according to this embodiment may contain the particles of the first and second active substances already in admixture. In such embodiment, means for mixing the two types of particles are not required.

In yet a further aspect the present invention provides a kit comprising:
a) a composition of matter according to the invention;
b) means for applying the composition of a) to a pest-infected environment; and
c) instructions for use.

The kits according to the invention may be used in agriculture as well as for human hygiene and/or health for example at homes and also in public places where presence of pests should be avoided or limited such as hospitals, schools, camps, hotels, hostels, dormitories, and also in airplanes, sea vessels, and the like.

FIG. 1 provides schematic illustration of a structure of a particle, first type and/or second type particle [100] comprised within the composition of matter according to one embodiment of the invention. The particle comprises a core of an active substance (first or second) [102]. The core is coated with a first coating layer [104]. In this specific embodiment the first coating layer is coated with a second coating layer [106]. In this specific embodiment the second coating layer is further coated with a third coating layer [108]. It is noted that in the figure the layers are perfectly (100%) superimposed. However, in some embodiments the layers may be partly superimposed e.g., the layers (first and/or second and/or third may be mixed with each other at least in part as noted herein above), and also they may be intermixed at least in part.

Figure 2:
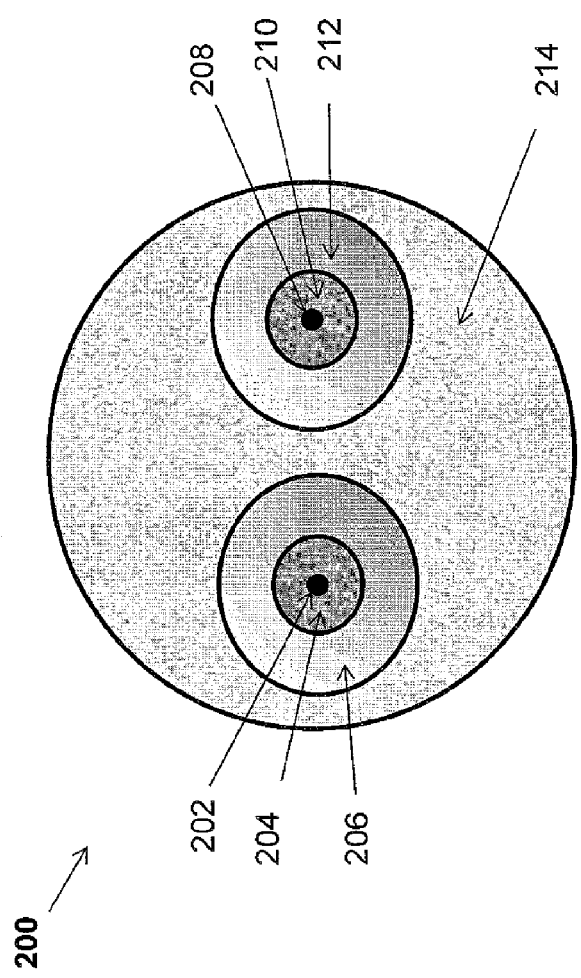

FIG. 2 provides schematic illustration of a particulate composition of matter according to one embodiment of the invention [200]. The composition comprises a first active substance [202] and a second active substance [208], the first and second active substances are each individually coated with a first coating layer [204] and [210], respectively. In this specific embodiment each of the first coating layers is coated with a second coating layer [206] and [212], respectively. The first and second active substances are further coated with a third coating layer [214]. It is noted that in FIG. 2 the first and the second layers coating each of the first and second active substances are perfectly (100%) superimposed. Also, the third coating layer is perfectly superimposed with the second layer. However, in some embodiments of the invention the layers (first, second and third) may be partly superimposed e.g., the first and second layers and/or the second and third layers and/or the first, second and third layers may be mixed with each other at least in part as detailed herein above. As may be illustrated from FIG. 2, the first active substance [202] and the second active substance [208] are each separately coated with first and second layers and are covered with the same third coating layer [214]. As shown in FIG. 2, the coating may be envisaged as a cover of any kind of shape.

Figure 3:
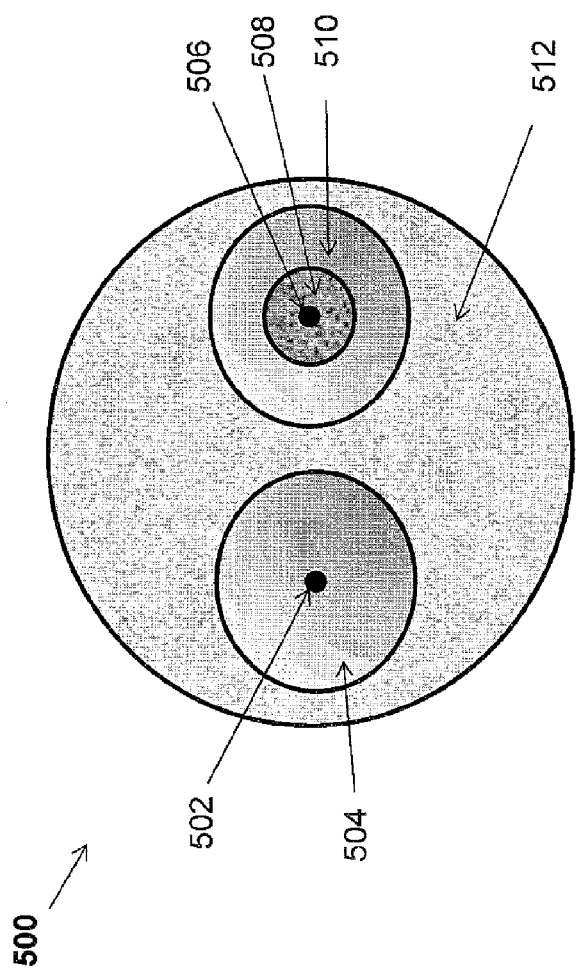

FIG. 3 provides schematic illustration of a particulate composition of matter according to one embodiment of the invention [500]. The composition comprises a first active substance [502] and a second active substance [506], the second active substance is coated with a first coating layer [508]. In this specific embodiment the second active substance is coated with a second coating layer [510]. The first active substance [502] is not coated with a first coating layer but with a second coating layer only [504]. The first and second active substances are further coated with a third coating layer [512]. It is noted that in FIG. 3 the various coating layers of the first and second active substances are perfectly (100%) superimposed. However, in some embodiments of the invention the layers (first and/or second and/or third) may be partly superimposed e.g., the first and second layers and/or the second and third layers and/or the first, second and third layers may be mixed with each other at least in part as detailed herein above. It is further noted that in FIG. 3 the thickness of the various coating layers e.g., the second coating layer of the first active substance, are provided herein only as an illustration and should not be limited to the proportions provided in the figure. The coating layers may be thinner or thicker. As illustrated in FIG. 3, the first active substance [502] and the second active substance [506] are covered with the same third coating layer [512]. As shown in FIG. 3, the coating may be envisaged as a cover of any kind of shape. It is noted that FIG. 3 illustrates an embodiment wherein only the second substance is coated with a first coating layer. In a similar manner an embodiment in which only the first active substance is coated with a first coating layer and the second active substance is not coated with a first coating layer but is directly coated with a second coating layer is within the scope of the present invention.

Figure 4:
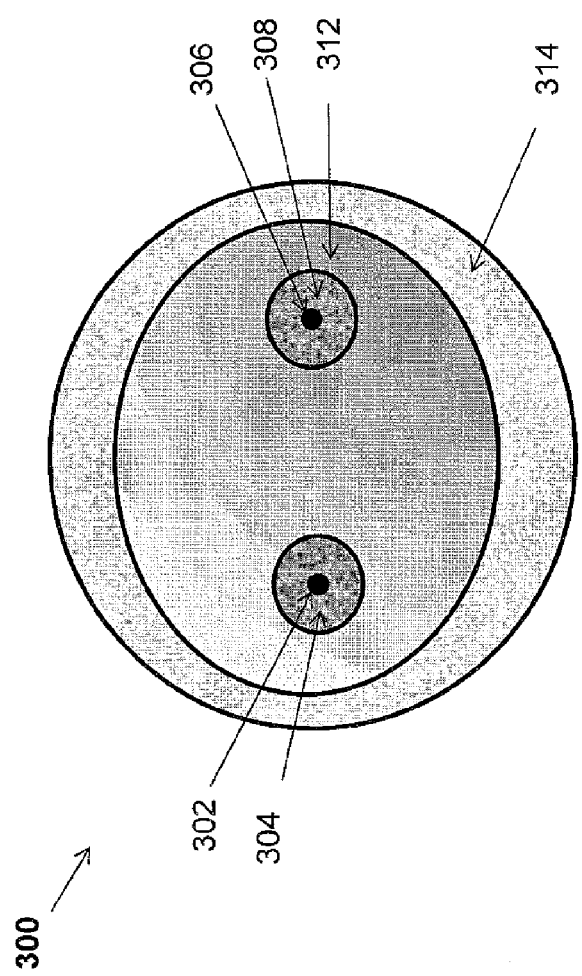

FIG. 4 provides schematic illustration of a particulate composition of matter according to one embodiment of the invention [300]. The composition comprises a first active substance [302] and a second active substance [306], the first and second active substances are each individually coated with a first coating layer [304] and [308], respectively. The first and second active substances are further coated with a second and third coating layer [312] and [314], respectively. It is noted that in FIG. 4 the various coating layers are perfectly (100%) superimposed. However, in some embodiments the layers may be partly superimposed e.g., the layers (first and/or second and/or third) may be mixed with each other at least in part as detailed herein above. As shown in FIG. 4, the first active substance [302] and the second active substance [306] are each separately coated with first layer [304] and [308], respectively and are both covered with the same second [312] and third [314] coatings layers. As shown in FIG. 4, the second [312] and a third [314] coating layers may be envisaged as a cover of any kind of shape. It is noted that FIG. 4 illustrates an embodiment wherein both the first and second coating layers are covered with a first coating layer. An embodiment in which only one of the first active or second active substances is coated with a first coating layer is within the scope of the present invention. To this end, covering only one of the first or second active substances with a first coating layer might be sufficient to prevent the contact between them in the composition according to the invention.

Figure 5:
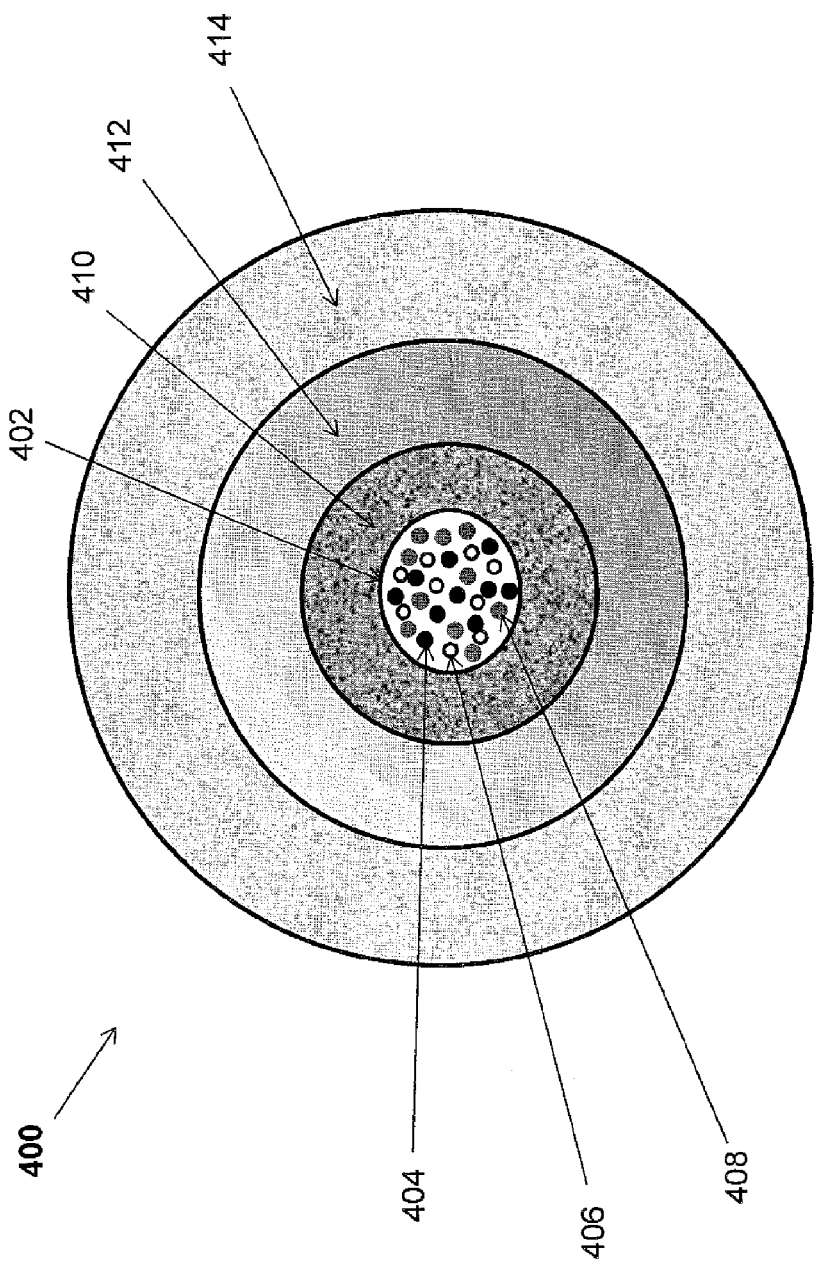

FIG. 5 provides a schematic illustration of a structure of a composition of matter [400] according to one embodiment of the invention. The composition comprises a core [402] of an admixture of a first functional substance [404], a second functional substance [406] and an inert additive [408]. The core of the composition may optionally further comprise at least one relaxant agent (not shown in the figure). It is noted that the first active substance and/or second active substance and/or the inert additive comprised within the core [402] may be in a physical contact with each other. It is further noted that for ease of illustration the core [402] is not fully occupied by the first and second active substances and additive. In the figure the core [402] is coated with a first coating layer [410]. In this specific embodiment the first coating layer is coated with a second coating layer [412]. In this specific embodiment the second coating layer is further coated with a third coating layer [414]. It is noted that in the figure the layers are perfectly (100%) superimposed. However, in some embodiments the layers may be partly superimposed e.g., the layers (first and/or second and/or third may be mixed with each other at least in part as noted herein above), and also they may be intermixed at least in part.

It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that features of certain embodiments of the invention which are described in detail in the context of one aspect of the invention, may be applicable in other aspects of the invention.

DESCRIPTION OF NON-LIMITING EXAMPLES

Reference is now made to the following non-limiting examples, which together with the above illustrate the invention in a non-limiting fashion.

In general, the following instrumentation was used in the various examples, when applicable: high pressure electric liquid sprayer, homogenizer, electric mixer, analytical scales, oven incubator and industrial food mixer.

It is noted that all of the ingredients used in the examples provided herein below were purchased from Depotchem (Israel) and were food grade certified products apart from boric acid which was certified as agriculture grade.

Example 1

Preparation of a Composition of Matter Comprising Acid and Base Particles a. Preparation of Particles of a First Type:

100 g of granular $NaHCO_3$ (sodium bicarbonate) were sprayed with a solution of 5 g of whey and 5 g of rice starch in 15 ml of water (first coating) followed by mixing for 5 minutes and drying at 39° C. for one hour.

The resulting mixture was sprayed with a solution of 5 g carboxymethyl cellulose (CMC) and 2 g of xanthan gum in 15 ml of water (second coating) followed by mixing for 5 minutes and drying at 39° C. for one hour.

The resulting mixture was sprayed with 5 g of glucose solution in 5 ml of water (third coating) followed by mixing for 5 minutes and drying at 39° C. for one hour.

b. Preparation of Particles of a Second Type:

74 g of granular $H_3BO_3$ (boric acid) were sprayed with a solution of 4 g whey and 4 g of rice starch in 12 ml of water (first coating) followed by mixing for 5 minutes and drying at 39° C. for one hour.

The resulting mixture was sprayed with a solution of 4 g CMC and 1.5 g xanthan gum in 12 ml of water (second coating) followed by mixing for 5 minutes and drying at 39° C. for one hour.

The resulting mixture was sprayed with a solution of 4 g glucose in 4 ml of water (third coating) followed by mixing for 5 minutes and drying at 39° C. for one hour.

c. Combining the Particles of a First and a Second Type:

The particles of the first and the second type prepared in items (a) and (b) above were mixed to produce a molar ratio of 1:1 between the first functional substance ($NaHCO_3$) and the second functional substance ($H_3BO_3$) followed by addition and mixing therewith the following additive ingredients: 20 g potatoes starch, 0.5 g NaCl, 0.2 g KCl, 20 g powdered sugar and 0.005 g butyric acid. The resulting composition of matter was in the form of a powder.

Example 2

Preparation of a Composition of Matter Comprising Acid and Base as Active Substances Under Controlled Humidity Conditions The following composition was prepared in a dry room with humidity conditions of about 20% to 30%.

Preparation of $HBO_2$

To produce 1.48 mole metaboric acid (i.e., 65 g, based on MW of 43.81 g/mole) 100 g agriculture grade boric acid were dried under dry room conditions by heating to a temperature of 170° C. for about 20 minutes. It is noted that in view of loss of material during the preparation process, the starting amount of the boric acid used in the preparation was slightly more than 1.48 moles (based on boric acid MW of 61.81 g/mole).

Preparation of the Composition:

100 g of granular $NaHCO_3$ (sodium bicarbonate), 65 g granular $HBO_2$ (metaboric acid) (as prepared above), 20 g $CaSO_4$ and 10 g KBr were dissolved in 200 g dehydrated ethanol and mixed for 15 minutes. The resulting mixture was dried in an oven at a temperature of 60° C. for a time period of 20 minutes. The dry mixture was ground to a powder.

The powder was sprayed with a solution of 4 g whey and 4 g rice starch in 15 ml of dehydrated ethanol (first coating) followed by mixing for 5 minutes and drying at 39° C. for one hour.

The resulting mixture was sprayed with a solution of 4 g carboxymethyl cellulose (CMC) and 1.5 g of xanthan gum in 15 ml of dehydrated ethanol (second coating) followed by mixing for 5 minutes and drying at 39° C. for one hour.

The resulting mixture was sprayed with 4 g of glucose solution in 5 ml of dehydrated ethanol (third coating) followed by mixing for 5 minutes and drying at 39° C. for one hour.

The resulting mixture was mixed with 20 g potatoes starch, 0.5 g NaCl, 0.2 g KCl, 20 g powdered sugar and 5 grams crystal menthol.

To maintain dry conditions the composition was kept under desiccated storage conditions.

Example 3

Pesticide Application

A powder applicator such as dust dispenser was used to apply the composition of matter according to the invention into cracks and places of deposit (infected loci). The amount applied was equal or less than five grams per square meter.

Example 4

Efficacy of the Composition of Matter According to the Invention Against Cockroaches The efficacy of the composition of matter according to the invention (as prepared in Example 1) against cockroaches of the species *Blatella Germanica* was compared with that of the pesticide "Maxforce®" (HF) 2.15% imidacloprid (Bayer AG) over the course of one month at room temperature.

Ten plastic containers covered with a virus net were used. The virus net was used in order to prevent small insects to penetrate and invest crops with viruses. 19 cockroaches were placed in each container together with egg trays (cardboard) and a continuous supply of cat food and sliced cucumbers refreshed every three days to ensure the food consumption. The food was provided in Petri test plates (Petri dishes). A tank containing 4 g pesticide was placed in the containers on top of the Petri dishes as far as possible from the food (it is noted that the pesticide was kept away from the food to show its qualities of attraction of itself and not consumed just because of its proximity to the food).

The various containers were marked as follows: A—fresh "Maxforce®", B—fresh composition of matter prepared according to Example 1, C—aged "Maxforce®" (kept at room temperature for a period of time of one month), D—aged composition of matter prepared according to Example 1 (kept at room temperature for a period of time of one month), E—control. The experiment was conducted twice.

During the experiment the number of dead cockroaches was counted and dead ones were removed. Newly hatched cockroaches were not counted.

Results of the number of dead cockroaches per day and a cumulative percentage are presented in Table 1 and Table 2, the latter representing the repetition experiment in which the various containers are marked as A', B', C', D' and E'.

TABLE 1

The number of dead cockroaches per day and cumulative percent dead

| E tank | | D tank | | C tank | | B tank | | A tank | | |
|---|---|---|---|---|---|---|---|---|---|---|
| dead % roaches | dead roaches | dead % roaches | dead roaches | dead % roaches | dead roaches | dead % roaches | dead roaches | dead % roaches | dead roaches | Test hour |
| 0 | 0 | 42.1 | 8 | 0 | 0 | 57.8 | 11 | 0 | 0 | ½ |
| 0 | 0 | 73.6 | 6 | 5.2 | 1 | 84.2 | 5 | 15.7 | 3 | 1 |
| 5.2 | 1 | 89.4 | 3 | 5.2 | 0 | 100 | 3 | 36.8 | 4 | 6 |
| 5.2 | 0 | 100 | 2 | 5.2 | 0 | 100 | 0 | 52.6 | 3 | 12 |
| 5.2 | 0 | 100 | 0 | 5.2 | 0 | 100 | 0 | 0 | 0 | 18 |
| 10.5 | 1 | 100 | 0 | 5.2 | 0 | 100 | 0 | 0 | 0 | 24 |
| 10.5 | 0 | 100 | 0 | 5.2 | 0 | 100 | 0 | 0 | 0 | 30 |
| 10.5 | 0 | 100 | 0 | 5.2 | 0 | 100 | 0 | 0 | 0 | 36 |
| 10.5 | 0 | 100 | 0 | 5.2 | 0 | 100 | 0 | 0 | 0 | 42 |
| 10.5 | 0 | 100 | 0 | 5.2 | 0 | 100 | 0 | 0 | 0 | 48 |

TABLE 2

The number of dead cockroaches per day and cumulative percent dead

| E' tank | | D' tank | | C' tank | | B' tank | | A' tank | | |
|---|---|---|---|---|---|---|---|---|---|---|
| dead % roaches | dead roaches | dead % roaches | dead roaches | dead % roaches | dead roaches | dead % roaches | dead roaches | dead % roaches | dead roaches | Test hour |
| 5.2 | 1 | 42.1 | 8 | 0 | 0 | 42.1 | 8 | 15.7 | 3 | ½ |
| 5.2 | 0 | 63.1 | 4 | 0 | 0 | 73.6 | 6 | 42.1 | 5 | 1 |
| 5.2 | 0 | 78.9 | 3 | 5.2 | 1 | 100 | 5 | 47.3 | 1 | 6 |
| 5.2 | 0 | 89.4 | 2 | 5.2 | 0 | 100 | 0 | 52.6 | 1 | 12 |
| 5.2 | 0 | 100 | 2 | 5.2 | 0 | 100 | 0 | 57.8 | 1 | 18 |
| 5.2 | 0 | 100 | 0 | 5.2 | 0 | 100 | 0 | 57.8 | 0 | 24 |
| 5.2 | 0 | 100 | 0 | 5.2 | 0 | 100 | 0 | 57.8 | 0 | 30 |
| 5.2 | 0 | 100 | 0 | 5.2 | 0 | 100 | 0 | 57.8 | 0 | 36 |
| 5.2 | 0 | 100 | 0 | 5.2 | 0 | 100 | 0 | 57.8 | 0 | 42 |
| 5.2 | 0 | 100 | 0 | 5.2 | 0 | 100 | 0 | 57.8 | 0 | 48 |

Graphic views of the average cumulative percentage of cockroaches eradicated in two trials are illustrated in FIG. 6A and FIG. 6B. In the figures the Y axis indicates the said percentage and the X axis indicates the time scale (0.5, 1, 6, 12 and 18 hours). The efficacy and superiority of the composition of matter according to the invention is evident from the experimental results. The results detailed in Tables 1 and 2 and depicted in FIG. 6A and FIG. 6B indicate that the use of the composition of matter according to the invention resulted in 100% death of the cockroaches within 6, 12 or 18 hours using both fresh and aged compositions while utilizing the "Maxforce®" pesticide resulted with a maximum mortality of 57.8% and only after 48 hours. At a time scale between 4 to 6 hours the cockroaches lost interest in the "Maxforce®" although it looked fresh. It is further noted that "Maxforce®" completely lost its lethality after storage of one month at room temperature conditions, and its effect was not distinct from the control group.

Without wishing to be bound by any theory, it is believed that the mortality observed in the control group probably resulted from a trauma caused by the transfer of the cockroaches to the containers however the number of the dead cockroaches in the control group is insignificant and does not add marginal additional parameter to the experimental results.

Despite some decline in the attraction of the cockroaches to the composition of matter according to the invention, the composition maintained its effectiveness over time. While the composition of matter according to the invention showed efficiency after one month of storage, "Maxforce®" had completely lost its capacity. It is noted in this respect that the composition of matter according to the invention withstands molds and microorganisms such as fungi and bacteria, and those cannot develop thereon.

Example 5

Efficacy of the Composition of Matter According to the Invention Against Small Pests The efficacy of the composition of matter according to the invention against field small pests such as slugs, crickets was tested. All (100%) the pests were eradicated within 24 hours from introduction of the product to their nest.

Example 6

Efficacy of the Composition of Matter According to the Invention Against Fleas

The efficacy of the composition of matter according to the invention against flea infestation in the farm at the Faculty of Agriculture in Rehovot, Israel (Hebrew University) was tested.

A variety of commercial pesticides (sanitary, veterinary) was used, inter-alia Frontline®, Advantage®, Polaris®, Tactics® and Sipermetrine®. All pesticides used showed temporary elimination efficiency level in goats infested with fleas, especially in the goat kids (data not shown). It is believed that the commercial chemical pesticides have not shown efficacy in eradicating the infestation due to high resistance of the insects thereto. These unsuccessful attempts led to the loss of generations of sheep and goats as a result of the flea infestation. The present inventors then tested the efficacy of the composition of matter of Example 1 against flea infestation in goats. After a period of intensive treatment the use of composition of matter according to the invention caused successful extermination of the pest.

Example 7

Preparation of a Composition of Matter Comprising Acid and Base Particles with Only First Type Particles Coated with a First Coating Layer a. Preparation of Particles of a First Type:

100 g of granular $NaHCO_3$ (sodium bicarbonate) are sprayed with a solution of 5 g of whey and 5 g of rice starch in 15 ml of water (first coating) followed by mixing for 5 minutes and drying at 39° C. for one hour.

The resulting mixture is sprayed with a solution of 5 g carboxymethyl cellulose (CMC) and 2 g of xanthan gum in 15 ml of water (second coating) followed by mixing for 5 minutes and drying at 39° C. for one hour.

The resulting mixture is sprayed with 5 g of glucose solution in 5 ml of water (third coating) followed by mixing for 5 minutes and drying at 39° C. for one hour.

b. Preparation of Particles of a Second Type:

74 g of granular $H_3BO_3$ (boric acid) are sprayed with a solution of 4 g CMC and 1.5 g xanthan gum in 12 ml of water (second coating) followed by mixing for 5 minutes and drying at 39° C. for one hour.

The resulting mixture is sprayed with a solution of 4 g glucose in 4 ml of water followed by mixing for 5 minutes and drying at 39° C. for one hour.

c. Combining the Particles of a First and a Second Type:

The particles of the first and the second type prepared in items (a) and (b) above are mixed to produce a molar ratio of 1:1 between the first functional substance ($NaHCO_3$) and the second functional substance ($H_3BO_3$) followed by addition and mixing therewith the following additive ingredients: 20 g potatoes starch, 0.5 g NaCl, 0.2 g KCl, 20 g powdered sugar and 0.005 g butyric acid.

Example 8

Preparation of a Composition of Matter Comprising $KMNO_4$ and Glycerol a. Preparation of Particles of a First Type:

About 200 g of glycerol provided in an adsorbed form on $CaCO_3$ (wherein in the adsorbed form the glycerol and $CaCO_3$ are present at 1:1 molar ratio i.e., about 100 g glycerol and about 100 g $CaCO_3$) are sprayed with a solution of 5 g of whey and 5 g of rice starch in 15 ml of water (first coating) followed by mixing for 5 minutes and drying at 39° C. for one hour.

The resulting mixture is sprayed with a solution of 5 g carboxymethyl cellulose (CMC) and 2 g of xanthan gum in 15 ml of water (second coating) followed by mixing for 5 minutes and drying at 39° C. for one hour.

The resulting mixture is sprayed with 5 g of glucose solution in 5 ml of water (third coating) followed by mixing for 5 minutes and drying at 39° C. for one hour.

b. Preparation of Particles of a Second Type:

About 75 g of $KMNO_4$ are sprayed with a solution of 4 g whey and 4 g of rice starch in 12 ml of water (first coating) followed by mixing for 5 minutes and drying at 39° C. for one hour.

The resulting mixture is sprayed with a solution of 4 g CMC and 1.5 g xanthan gum in 12 ml of water (second coating) followed by mixing for 5 minutes and drying at 39° C. for one hour.

The resulting mixture is sprayed with a solution of 4 g glucose in 4 ml of water (third coating) followed by mixing for 5 minutes and drying at 39° C. for one hour.

c. Combining the Particles of a First and a Second Type:

The particles of the first and the second type prepared in items (a) and (b) above are followed by addition and mixing therewith the following additive ingredients: 20 g potatoes starch, 0.5 g NaCl, 0.2 g KCl, 20 g powdered sugar and 0.005 g butyric acid. The resulting composition of matter is in the form of a powder.

Example 9

Preparation of a Composition of Matter Comprising $KMNO_4$ and Glycerol Wherein Only $KMNO_4$ is Coated with a First Coating Layer a. Preparation of Particles of a First Type:

About 200 g of glycerol provided in an adsorbed form on $CaCO_3$ (wherein in the adsorbed form the glycerol and $CaCO_3$ are present at 1:1 molar ratio i.e., about 100 g glycerol and about 100 g $CaCO_3$) are sprayed with a solution of 5 g carboxymethyl cellulose (CMC) and 2 g of xanthan gum in 15 ml of water (second coating) followed by mixing for 5 minutes and drying at 39° C. for one hour.

The resulting mixture is sprayed with 5 g of glucose solution in 5 ml of water (third coating) followed by mixing for 5 minutes and drying at 39° C. for one hour.

b. Preparation of Particles of a Second Type:

About 75 g of $KMNO_4$ are sprayed with a solution of 4 g whey and 4 g of rice starch in 12 ml of water (first coating) followed by mixing for 5 minutes and drying at 39° C. for one hour.

The resulting mixture is sprayed with a solution of 4 g CMC and 1.5 g xanthan gum in 12 ml of water (second coating) followed by mixing for 5 minutes and drying at 39° C. for one hour.

The resulting mixture is sprayed with a solution of 4 g glucose in 4 ml of water (third coating) followed by mixing for 5 minutes and drying at 39° C. for one hour.

c. Combining the Particles of a First and a Second Type:

The particles of the first and the second type prepared in items (a) and (b) above are followed by addition and mixing therewith the following additive ingredients: 20 g potatoes starch, 0.5 g NaCl, 0.2 g KCl, 20 g powdered sugar and 0.005 g butyric acid. The resulting composition of matter is in the form of a powder.

Example 10

Efficacy Against Cockroaches of the Composition of Matter Comprising $KMNO_4$ and Glycerol The efficacy of the composition of matter of Examples 8-9 against cockroaches of the species *Blatella Germanica* is compared with that of a known pesticide e.g., the pesticide "Maxforce®" (HF) 2.15% imidacloprid (Bayer AG) over the course of several time periods e.g., one month and at room temperature.

Ten plastic containers covered with a virus net are used. Cockroaches are placed in each container together with egg trays (cardboard) and a continuous supply of cat food and sliced cucumbers refreshed every three days to ensure the food consumption. The food is provided in Petri test plates (Petri dishes). A tank containing 4 g pesticide is placed in the containers on top of the Petri dishes as far as possible from the food.

The various containers are marked as follows: A—fresh "Maxforce®", B—fresh composition of matter prepared according to Examples 8-9, C—aged "Maxforce®" (kept at room temperature for a period of time of e.g., one month), D—aged composition of matter prepared according to Examples 8-9 (kept at room temperature for a period of time of e.g., one month), E—control. The experiments are conducted twice (the repetition experiment in which the various containers are marked as A', B', C', D' and E').

During the experiment the number of dead cockroaches is counted and dead ones are removed. Newly hatched cockroaches are not counted.

ILLUSTRATIVE EMBODIMENTS

The following embodiments are illustrative and not intended to limit the claimed subject matter.

Embodiment 1

A pesticidal particulate composition of matter comprising individually coated first active substance and individually coated second active substance, wherein said first and second active substances form a gaseous product upon contact with each other within a pest body (said contact optionally leads to an exothermic reaction generating heat) and wherein said gaseous product being capable of destroying said pest.

Embodiment 2

The pesticidal particulate composition according to embodiment 1, wherein each of said first and second individually coated active substances is contained in first and second type particles, respectively.

Embodiment 3

The pesticidal particulate composition according to embodiment 1, wherein both said individually coated first and second active substances are contained in the same particle.

Embodiment 4

The pesticidal particulate composition according to any one of embodiments 1 to 3 wherein said first active substance is an acidic substance.

Embodiment 5

The pesticidal particulate composition according to embodiment 4, wherein said acidic substance is selected from the group consisting of boric acid, metaboric acid, formic acid, citric acid glycerin and any combination of the same.

Embodiment 6

The pesticidal particulate composition according to embodiment 5, wherein said acidic substance is boric acid ($H_3BO_3$).

Embodiment 7

The pesticidal particulate composition according to embodiment 5, wherein said acidic substance is metaboric acid ($HBO_2$).

Embodiment 8

The pesticidal particulate composition according to any one of embodiments 1 to 7, wherein said second active substance is a basic substance.

Embodiment 9

The pesticidal particulate composition according to embodiment 8, wherein said basic substance is selected from the group consisting of $NaHCO_3$, $CaCO_3$, $KMnO_4$ and any combination of the same.

Embodiment 10

The pesticidal particulate composition according to embodiment 9, wherein said basic substance is sodium bicarbonate.

Embodiment 11

The pesticidal particulate composition according to any one of embodiments 1 to 3, wherein said first active substance is an acidic substance and said second active substance is a basic substance.

Embodiment 12

The pesticidal particulate composition according to embodiment 11 wherein said acidic substance is boric acid and said basic substance is $NaHCO_3$ which upon contact (e.g., in a substantially aqueous environment) form $CO_2$ gas.

Embodiment 13

The pesticidal particulate composition according to embodiment 11 wherein said acidic substance is metaboric acid and said basic substance is $NaHCO_3$ which upon contact (e.g., in a substantially aqueous environment) form $CO_2$ gas.

Embodiment 14

The pesticidal particulate composition according to any one of embodiments 1 to 13, wherein said first active substance and said second active substance are present in said composition at a ratio in accordance with the stoichiometry of the reaction between them upon contacting each other (e.g., in a substantially aqueous environment).

Embodiment 15

The pesticidal particulate composition according to any of embodiments 1 to 14, wherein said first active substance and said second active substance are present in said composition at a an equimolar ratio (1:1).

Embodiment 16

The pesticidal particulate composition according to any one of embodiments 1 to 15, wherein said first active substance and said second active substance are each individually coated at least in part with a first coating layer.

Embodiment 17

The pesticidal particulate composition according to embodiment 16, wherein said first coating layer comprises at least one material which prevents contact between said first active substance and said second active substance, which material disintegrates at least in part in a substantially aqueous environment thereby enabling contact between said first active substance and said second active substance.

Embodiment 18

The pesticidal particulate composition according to embodiment 16, wherein the said material in the first coating layer of the first active substance and in the first coating layer of the second active substance may be the same or different.

Embodiment 19

The pesticidal particulate composition according to any one of embodiments 17 or 18, wherein said material is selected from the group consisting of proteins, carbohydrates, nutrients synthetic materials and any combination of the same.

Embodiment 20

The pesticidal particulate composition according to embodiment 19, wherein said protein is selected from the group consisting of dairy proteins, meat proteins, egg proteins, plant proteins and any combination of the same.

Embodiment 21

The pesticidal particulate composition according to embodiment 20, wherein said protein is whey protein.

Embodiment 22

The pesticidal particulate composition according to any one of embodiments 16 to 21, wherein said material is an hygroscopic material.

Embodiment 23

The pesticidal particulate composition according to embodiment 22, wherein said hygroscopic material is rice starch.

Embodiment 24

The pesticidal particulate composition according to any one of embodiments 16 to 22, wherein said first coating layer comprises at least one whey protein and rice starch.

Embodiment 25

The pesticidal particulate composition according to any one of embodiments 16 to 24, wherein at least one of said first active substance and said second active substance is further coated at least in part with a same or different second coating layer.

Embodiment 26

The pesticidal particulate composition according to embodiment 25, wherein said second coating layer comprises at least one material selected from the group consisting of a foaming agent, a swelling agent, adhesive agent, anti-coalescence agent and any combination of the same.

Embodiment 27

The pesticidal particulate composition according to embodiment 26, wherein said material in the second coating layer of the first active substance and in the second coating layer of the second active substance may be the same or different.

Embodiment 28

The pesticidal particulate composition according to embodiment 26, wherein said adhesive agent is selected from the group consisting of xanthan gum, guar gum and any combination of the same.

Embodiment 29

The pesticidal particulate composition according to embodiment 26, wherein said foaming agent is carboxymethyl cellulose (CMC).

Embodiment 30

The pesticidal particulate composition according to embodiment 26, wherein said second coating layer comprises carboxymethyl cellulose (CMC) and xanthan gum.

Embodiment 31

The pesticidal particulate composition according to any one of embodiments 25 to 30, wherein at least one of said first active substance and said second active substance is further coated with a third coating layer, wherein said third coating layer comprises at least one specific insect attractant.

Embodiment 32

The pesticidal particulate composition according to embodiment 31, wherein said specific insect attractant in said third coating layer of the at least one of said first active substance and said second active substance may be the same or different.

Embodiment 33

The pesticidal particulate composition according to embodiment 31 or 32, wherein said insect attractant is a flavoring agent, a pest/insect baiting agent or any combination of the same.

Embodiment 34

The pesticidal particulate composition according to embodiment 33, wherein said flavoring agent is sugar (e.g., a sugar prepared from a sugar cane).

Embodiment 35

The pesticidal particulate composition according to embodiment 34, wherein said sugar is glucose.

Embodiment 36

The pesticidal particulate composition according to embodiment 33, wherein said baiting agent is a fragrance or a pheromone.

Embodiment 37

The pesticidal particulate composition according to embodiment 31, wherein said at least one insect attractant is selected from the group consisting of wood powder starch, dry bone powder, peanut powder, milk powder, vegetable powder, lactic acid, dead yeast powder, fish powder and any combination of the same.

Embodiment 38

The pesticidal particulate composition according to any one of the preceding embodiments, wherein said composition further comprises at least one additive.

Embodiment 39

The pesticidal particulate composition according to embodiment 38, wherein said at least one additive is selected from the group consisting of potato starch, sugar, salt, butyric acid and any combination of at least two of them.

Embodiment 40

The pesticidal particulate composition according to embodiment 39, wherein said additive is a combination of at least two of any of potato starch, powdered sugar, NaCl, KCl and butyric acid.

Embodiment 41

A pesticidal particulate composition of matter comprising particles, the particles comprising a first active substance, a second active substance, at least one inert additive and optionally at least one relaxant agent, wherein inside a pest body (e.g., in the aqueous environment therein) the first and second active substances form a gaseous product, the gaseous product being capable of destroying the pest.

Embodiment 42

A pesticidal particulate composition of matter comprising particles, the particles comprising a first active substance, a second active substance and at least one inert additive, wherein inside a pest body (e.g., in the aqueous environment therein) the first and second active substances form a gaseous product, the gaseous product being capable of destroying the pest.

Embodiment 43

The pesticidal particulate composition according to any one of embodiments 41 or 42 wherein said first active substance is an acidic substance.

Embodiment 44

The pesticidal particulate composition according to any one of embodiments 41 to 43, wherein said acidic substance is selected from the group consisting of boric acid, metaboric acid, formic acid, citric acid glycerin and any combination of the same.

Embodiment 45

The pesticidal particulate composition according to embodiment 43, wherein said acidic substance is boric acid ($H_3BO_3$).

Embodiment 46

The pesticidal particulate composition according to embodiment 43, wherein said acidic substance is metaboric acid ($HBO_2$).

Embodiment 47

The pesticidal particulate composition according to any one of embodiments 41 to 46, wherein said second active substance is a basic substance.

Embodiment 48

The pesticidal particulate composition according to embodiment 47, wherein said basic substance is selected from the group consisting of $NaHCO_3$, $CaCO_3$, $KMnO_4$ and any combination of the same.

Embodiment 49

The pesticidal particulate composition according to embodiment 48, wherein said basic substance is sodium bicarbonate.

Embodiment 50

The pesticidal particulate composition according to any one of embodiments 41 or 42, wherein said first active substance is an acidic substance and said second active substance is a basic substance.

Embodiment 51

The pesticidal particulate composition according to embodiment 50 wherein said acidic substance is boric acid and said basic substance is $NaHCO_3$ which upon contact (e.g., in a substantially aqueous environment) form $CO_2$ gas.

Embodiment 52

The pesticidal particulate composition according to embodiment 50 wherein said acidic substance is metaboric acid and said basic substance is $NaHCO_3$ which upon contact (e.g., in a substantially aqueous environment) form $CO_2$ gas.

Embodiment 53

The pesticidal particulate composition according to any one of embodiments 41 to 52, wherein said first active substance and said second active substance are present in said composition at a ratio in accordance with the stoichiometry of the reaction between them upon contacting each other (e.g., in a substantially aqueous environment).

Embodiment 54

The pesticidal particulate composition according to any of embodiments 41 to 52, wherein said first active substance and said second active substance are present in said composition at a an equimolar ratio (1:1).

Embodiment 55

The pesticidal particulate composition according to any one of embodiments 41 to 54, wherein said particles are coated with a first coating layer.

Embodiment 56

The pesticidal particulate composition according to embodiment 55, wherein said first coating layer comprises at least one material which disintegrates at least in part in a substantially aqueous environment thereby enabling exposure of said first and second active substances to the aqueous environment in a pest body.

Embodiment 57

The pesticidal particulate composition according embodiment 56, wherein said material is selected from the group consisting of proteins, carbohydrates, nutrients, synthetic materials and any combination of the same.

Embodiment 58

The pesticidal particulate composition according to embodiment 57, wherein said protein is selected from the group consisting of dairy proteins, meat proteins, egg proteins, plant proteins and any combination of the same.

Embodiment 59

The pesticidal particulate composition according to embodiment 57, wherein said protein is whey protein.

Embodiment 60

The pesticidal particulate composition according to any one of embodiments 56 to 59, wherein said material is a hygroscopic material.

Embodiment 61

The pesticidal particulate composition according to embodiment 60, wherein said hygroscopic material is rice starch.

Embodiment 62

The pesticidal particulate composition according to any one of embodiments 55 to 60, wherein said first coating layer comprises at least one whey protein and rice starch.

Embodiment 63

The pesticidal particulate composition according to any one of embodiments 55 to 62, wherein said particles are further coated at least in part with a second coating layer.

Embodiment 64

The pesticidal particulate composition according to embodiment 63, wherein said second coating layer comprises at least one material selected from the group consisting of a foaming agent, a swelling agent, adhesive agent, anti-coalescence agent and any combination of the same.

Embodiment 65

The pesticidal particulate composition according to embodiment 64, wherein said adhesive agent is selected from the group consisting of xanthan gum, guar gum and any combination of the same.

Embodiment 66

The pesticidal particulate composition according to embodiment 64, wherein said foaming agent is carboxymethyl cellulose (CMC).

Embodiment 67

The pesticidal particulate composition according to embodiment 63, wherein said second coating layer comprises carboxymethyl cellulose (CMC) and xanthan gum.

Embodiment 68

The pesticidal particulate composition according to any one of embodiments 55 to 67, wherein said particles are further coated at least in part with a third coating layer, wherein said third coating layer comprises at least one specific insect attractant.

Embodiment 69

The pesticidal particulate composition according to embodiment 68, wherein said insect attractant is a flavoring agent, a pest/insect baiting agent or any combination of the same.

Embodiment 70

The pesticidal particulate composition according to embodiment 69, wherein said flavoring agent is sugar (e.g., a sugar prepared from a sugar cane).

Embodiment 71

The pesticidal particulate composition according to embodiment 70, wherein said sugar is glucose.

Embodiment 72

The pesticidal particulate composition according to embodiment 69, wherein said baiting agent is a fragrance or a pheromone.

Embodiment 73

The pesticidal particulate composition according to embodiment 68, wherein said at least one insect attractant is selected from the group consisting of wood powder starch, dry bone powder, peanut powder, milk powder, vegetable powder, lactic acid, dead yeast powder, fish powder and any combination of the same.

Embodiment 74

The pesticidal particulate composition according to any one of embodiments 41 to 73, wherein said composition further comprises at least one additive.

Embodiment 75

The pesticidal particulate composition according to embodiment 74, wherein said at least one additive is selected from the group consisting of potato starch, sugar, salt, crystal menthol and any combination of at least two of them.

Embodiment 76

The pesticidal particulate composition according to embodiment 74, wherein said additive is a combination of at least two of any of potato starch, powdered sugar, NaCl, KCl and crystal methanol.

Embodiment 77

The pesticidal particulate composition according to any one of embodiments 41 to 76, wherein said inert additive is selected from the group consisting of $CaSO_4$, CaO and any combination of the same.

Embodiment 78

The pesticidal particulate composition according to embodiment 77, wherein said inert additive is a $CaSO_4$.

Embodiment 79

The pesticidal particulate composition according to embodiment 42, wherein said relaxant agent is KBr.

Embodiment 80

A pesticidal composition of matter comprising a mixture of particles of a first type and particles of a second type, each particle comprising a core of an active substance, individually coated at least in part with a first coating layer, wherein
 the core of said first type particles comprises a first functional substance and the core of said second type particles comprises a second functional substance, said first and second functional substances forming a gaseous product upon contact with each other, said contact optionally leads to an exothermic reaction generating heat, wherein at least part of said gaseous product is in the form of gas bubbles;
 wherein the first coating layer comprises at least one material which prevents contact between said first and said second functional substance, which material disintegrates at least in part in a substantially aqueous environment to thereby enable contact between said first functional substance and said second functional substance, wherein the said material in the first coating layer of the first type particles and in the first coating layer of the second type particles may be the same or different; and
 wherein optionally at least one of said first type particles and said second type particles further comprise a second coating layer which may be superimposed at least in part with the said first coating layer, wherein said second layer comprises a material which prevents coalescence of the gas bubbles formed by the contact between said first functional substance and said second functional substance, wherein the said material in the second coating layer of the first type particles and in the second coating layer of the second type particles may be the same or different.

Embodiment 81

The pesticidal composition of according to embodiment 80, wherein at least one of said first type particles and said second type particles further comprise a third coating layer which may be superimposed with at least one of said first and second coating layers, wherein said third coating layer comprises at least one specific insect attractant, wherein the said specific insect attractant in the third coating layer of the at least one of said first type particles and said second type particles may be the same or different.

Embodiment 82

The pesticidal composition according to any one of embodiments 80 or 81, wherein said composition further comprises at least one additive.

Embodiment 83

The pesticidal composition according to any one of the embodiments 80 to 82, wherein said material which prevents contact between said first and said second functional substance comprised in said first coating layer is selected from the group consisting of proteins, carbohydrates, nutrients, synthetic materials and any combination of the same.

Embodiment 84

The pesticidal composition according to embodiment 83, wherein said protein is selected from the group consisting of dairy proteins, meat proteins, egg proteins, plant proteins and any combination of the same.

Embodiment 85

The pesticidal composition according to embodiment 83, wherein said protein is whey protein.

Embodiment 86

The pesticidal composition according to any one of embodiments 80 to 85, wherein said material is a hygroscopic material.

Embodiment 87

The pesticidal composition according to embodiment 86, wherein said material hygroscopic material is rice starch.

Embodiment 88

The pesticidal composition according to any one of embodiments 80 to 86, wherein said first layer comprises at least one whey protein and rice starch.

Embodiment 89

The pesticidal composition according to any one of embodiments 80 to 88 wherein said first functional substance is an acidic substance.

Embodiment 90

The pesticidal composition according to embodiment 89, wherein said acidic substance is selected from the group consisting of boric acid, metaboric acid, formic acid, citric acid glycerin and any combination of the same.

Embodiment 91

The pesticidal composition according to embodiment 89, wherein said acidic substance is boric acid ($H_3BO_3$).

Embodiment 92

The pesticidal composition according to embodiment 89, wherein said acidic substance is metaboric acid ($HBO_2$).

Embodiment 93

The pesticidal composition according to any one of embodiments 80 to 92, wherein said second functional substance is a basic substance.

Embodiment 94

The pesticidal composition according to embodiment 93, wherein said basic substance is selected from the group consisting of $NaHCO_3$, $CaCO_3$, $KMnO_4$ and any combination of the same.

Embodiment 95

The pesticidal composition according to embodiment 93, wherein said basic substance is sodium bicarbonate.

Embodiment 96

The pesticidal composition according to any one of embodiments 80 to 88, wherein said first active substance is an acidic substance and said second active substance is a basic substance.

Embodiment 97

The pesticidal composition according to embodiment 96 wherein said acidic substance is boric acid and said basic substance is $NaHCO_3$ which upon contact form $CO_2$ gas.

Embodiment 98

The pesticidal composition according to embodiment 96 wherein said acidic substance is metaboric acid and said basic substance is $NaHCO_3$ which upon contact form $CO_2$ gas.

Embodiment 99

The pesticidal composition according to any one of embodiments 80 to 98, wherein said second coating layer comprises at least one material selected from the group consisting of a foaming agent, a swelling agent, adhesive agent (e.g., a gum), anti-coalescence agent and any combination of the same.

Embodiment 100

The pesticidal composition according to embodiment 99, wherein said adhesive agent is selected from the group consisting of xanthan gum, guar gum and any combination of the same.

Embodiment 101

The pesticidal composition according to embodiment 100, wherein said foaming agent is carboxymethyl cellulose (CMC).

Embodiment 102

The pesticidal composition according to embodiment 100, wherein said adhesive agent is xanthan gum or guar gum.

Embodiment 103

The pesticidal composition according to any one of embodiments 80 to 100, wherein said second coating layer comprises carboxymethyl cellulose (CMC) and xanthan gum.

Embodiment 104

The pesticidal composition according to embodiment 81, wherein said insect attractant is a flavoring agent, a pest/insect baiting agent or any combination of the same.

Embodiment 105

The composition according to embodiment 104, wherein said flavoring agent is sugar (e.g., a sugar produced from a sugar cane).

Embodiment 106

The pesticidal composition according to embodiment 105, wherein said sugar is glucose.

Embodiment 107

The pesticidal composition according to embodiment 104, wherein said baiting agent is a fragrance or a pheromone.

Embodiment 108

The pesticidal composition according to embodiment 81, wherein said at least one insect attractant is selected from the group consisting of wood powder starch, dry bone powder, peanut powder, milk powder, vegetable powder, lactic acid, dead yeast powder, fish powder and any combination of the same.

Embodiment 109

The pesticidal composition according to embodiment 82, wherein said at least one additive is selected from the group consisting of potato starch, sugar, salt, butyric acid and any combination of at least two of them.

Embodiment 110

The pesticidal composition according to embodiment 82, wherein said additive is a combination of at least two of any of potato starch, powdered sugar, NaCl, KCl and butyric acid.

Embodiment 111

The pesticidal composition according to embodiment 82, wherein said additive is a combination of at least two of any of potato starch, powdered sugar, NaCl, KCl and crystal methanol.

Embodiment 112

The pesticidal composition according to any one of embodiment 80 to 111, wherein said particles of a first type and particles of a second type are mixed at a ratio that provides a molar ratio between the said first active substance and the said second active substance of about 1:1.

Embodiment 113

A pesticidal particulate composition of matter comprising a first functional substance and a second functional substance, wherein said first and second functional substances are each individually coated at least in part with a first coating layer;
  wherein said first and second functional substances form a gaseous product upon contact with each other (said contact optionally leads to an exothermic reaction generating heat), wherein at least part of said gaseous product is in the form of gas bubbles;
  wherein the first coating layer comprises at least one material which prevents contact between said first and said second functional substance, which material disintegrates at least in part in a substantially aqueous environment thereby enabling contact between said first functional substance and said second functional substance, wherein the said material in the first coating layer of the first active substance and in the first coating layer of the second active substance may be the same or different;
  wherein at least one of said first functional substance and said second functional substance is optionally further coated at least in part with same or different second coating layer wherein said second coating layer comprises a material which prevents coalescence of the gas bubbles formed by the contact between said first functional substance and said second functional substance, wherein the said material in the second coating layer of the first functional substance and in the second coating layer of the second functional substance may be the same or different; and
  wherein said first and second active substances are contained in a same particle.

Embodiment 114

The pesticidal particulate composition of according to embodiment 113, wherein at least one of said first functional substance and said second functional substance is further coated with a same or different third coating layer wherein said third coating layer comprises at least one specific insect attractant, wherein the said specific insect attractant in the third coating layer of the at least one of said first functional substance and said second functional substance may be the same or different.

Embodiment 115

The pesticidal particulate composition according to any one of embodiments 113 or 114, wherein said composition further comprises at least one additive.

Embodiment 116

The pesticidal particulate composition according to any one of the embodiments 113 to 115, wherein said material which prevents contact between said first and said second functional substance comprised in said first coating layer is selected from the group consisting of proteins, carbohydrates, nutrients synthetic materials and any combination of the same.

Embodiment 117

The pesticidal particulate composition according to embodiment 116, wherein said protein is selected from the group consisting of dairy proteins, meat proteins, egg proteins, plant proteins and any combination of the same.

Embodiment 118

The pesticidal particulate composition according to embodiment 117, wherein said protein is whey protein.

Embodiment 119

The pesticidal particulate composition according to any one of embodiments 113 to 118, wherein said material is a hygroscopic material.

Embodiment 120

The pesticidal particulate composition according to embodiment 119, wherein said hygroscopic material is rice starch.

Embodiment 121

The pesticidal particulate composition according to any one of embodiments 113 to 117, wherein said first layer comprises at least one whey protein and rice starch.

Embodiment 122

The pesticidal particulate composition according to any one of embodiments 113 to 121 wherein said first functional substance is an acidic substance.

Embodiment 123

The pesticidal composition according to embodiment 122, wherein said acidic substance is selected from the group consisting of boric acid, metaboric acid, formic acid, citric acid glycerin and any combination of the same.

Embodiment 124

The pesticidal particulate composition according to embodiment 122, wherein said acidic substance is boric acid ($H_3BO_3$).

Embodiment 125

The pesticidal particulate composition according to embodiment 122, wherein said acidic substance is metaboric acid ($HBO_2$).

Embodiment 126

The pesticidal particulate composition according to any one of embodiments 113 to 125, wherein said second functional substance is a basic substance.

Embodiment 127

The pesticidal particulate composition according to embodiment 126, wherein said basic substance is selected from the group consisting of $NaHCO_3$, $CaCO_3$, $KMnO_4$ and any combination of the same.

Embodiment 128

The pesticidal particulate composition according to embodiment 127, wherein said basic substance is sodium bicarbonate.

Embodiment 129

The pesticidal particulate composition according to any one of embodiments 113 to 121, wherein said first active substance is an acidic substance and said second active substance is a basic substance.

Embodiment 130

The pesticidal particulate composition according to embodiment 129 wherein said acidic substance is boric acid and said basic substance is $NaHCO_3$ which upon contact form $CO_2$ gas.

Embodiment 131

The pesticidal particulate composition according to embodiment 129 wherein said acidic substance is metaboric acid and said basic substance is $NaHCO_3$ which upon contact form $CO_2$ gas.

Embodiment 132

The pesticidal particulate composition according to any one of embodiments 113 to 131, wherein said second coating layer comprises at least one material selected from the group consisting of a foaming agent, a swelling agent, adhesive agent (e.g., a gum), anti-coalescence agent and any combination of the same.

Embodiment 133

The pesticidal particulate composition according to embodiment 132, wherein said adhesive agent is selected from the group consisting of xanthan gum, guar gum and any combination of the same.

Embodiment 134

The pesticidal particulate composition according to embodiment 132, wherein said foaming agent is carboxymethyl cellulose (CMC).

Embodiment 135

The pesticidal particulate composition according to embodiment 132, wherein said adhesive agent is Xanthan gum or guar gum.

Embodiment 136

The pesticidal particulate composition according to any one of embodiments 113 to 132, wherein said second coating layer comprises carboxymethyl cellulose (CMC) and xanthan gum.

Embodiment 137

The pesticidal particulate composition according to embodiment 114, wherein said insect attractant is a flavoring agent, a pest/insect baiting agent or any combination of the same.

Embodiment 138

The pesticidal particulate composition according to embodiment 137, wherein said flavoring agent is sugar (e.g., a sugar produced from a sugar cane).

Embodiment 139

The pesticidal particulate composition according to embodiment 138, wherein said sugar is glucose.

Embodiment 140

The pesticidal particulate composition according to embodiment 137, wherein said baiting agent is a fragrance or a pheromone.

Embodiment 141

The pesticidal particulate composition according to embodiment 114, wherein said at least one insect attractant is selected from the group consisting of wood powder starch, dry bone powder, peanut powder, milk powder, vegetable powder, lactic acid, dead yeast powder, fish powder and any combination of the same.

Embodiment 142

The pesticidal particulate composition according to embodiment 115, wherein said at least one additive is selected from the group consisting of potato starch, sugar, salt, butyric acid and any combination of at least two of them.

Embodiment 143

The pesticidal particulate composition according to claim 115, wherein said additive is a combination of at least two of any of potato starch, powdered sugar, NaCl, KCl and butyric acid.

Embodiment 144

The pesticidal particulate composition according to any one of embodiment 113 to 143, wherein said first functional substance and said second functional substance are present in said composition at a ratio in accordance with the stoichiometry of the reaction between them upon contacting each other.

Embodiment 145

The pesticidal particulate composition according to any one of embodiment 113 to 144, wherein said first active substance and said second active substance are present in said composition at a an equimolar ratio (1:1).

Embodiment 146

A pesticidal particulate composition of matter comprising particles, the particles comprising a core of an admixture of a first functional substance, a second functional substance, at least one inert additive and optionally at least one relaxant agent, wherein each said core is coated at least in part with a first coating layer;
   wherein said first and second functional substances form a gaseous product in the aqueous environment inside a pest body, wherein at least part of the gaseous product is in the form of gas bubbles;
   wherein the first coating layer comprises at least one material which disintegrates at least in part in a substantially aqueous environment to thereby enable exposure of the first functional substance and the second functional substance to the aqueous environment inside a pest body;
   wherein each of said particle is optionally further coated at least in part with a second coating layer wherein the second coating layer comprises a material which prevents coalescence of the gas bubbles formed at least in part by the first functional substance and the second functional substance.

Embodiment 147

The pesticidal particulate composition of according to embodiment 146, wherein said core is further coated with a third coating layer wherein said third coating layer comprises at least one specific insect attractant.

Embodiment 148

The pesticidal particulate composition according to any one of embodiments 146 or 147, wherein said composition further comprises at least one additive.

Embodiment 149

The pesticidal particulate composition according to any one of the embodiments 146 to 148, wherein said material which disintegrates at least in part in a substantially aqueous environment is selected from the group consisting of proteins, carbohydrates, synthetic materials and any combination of the same.

Embodiment 150

The pesticidal particulate composition according to embodiment 149, wherein said protein is selected from the group consisting of dairy proteins, meat proteins, egg proteins, plant proteins and any combination of the same.

Embodiment 151

The pesticidal particulate composition according to embodiment 149, wherein said protein is whey protein.

Embodiment 152

The pesticidal particulate composition according to any one of embodiments 146 to 151, wherein said material is a hygroscopic material.

Embodiment 153

The pesticidal particulate composition according to embodiment 152, wherein said hygroscopic material is rice starch.

Embodiment 154

The pesticidal particulate composition according to any one of embodiments 146 to 150, wherein said first layer comprises at least one whey protein and rice starch.

Embodiment 155

The pesticidal particulate composition according to any one of embodiments 146 to 154 wherein said first functional substance is an acidic substance.

Embodiment 156

The pesticidal particulate composition according to embodiment 155, wherein said acidic substance is selected from the group consisting of boric acid, metaboric acid, formic acid, citric acid glycerin and any combination of the same.

Embodiment 157

The pesticidal particulate composition according to embodiment 155, wherein said acidic substance is boric acid ($H_3BO_3$).

Embodiment 158

The pesticidal particulate composition according to embodiment 155, wherein said acidic substance is metaboric acid ($HBO_2$).

Embodiment 159

The pesticidal particulate composition according to any one of embodiments 146 to 158, wherein said second functional substance is a basic substance.

Embodiment 160

The pesticidal particulate composition according to embodiment 159, wherein said basic substance is selected from the group consisting of $NaHCO_3$, $CaCO_3$, $KMnO_4$ and any combination of the same.

Embodiment 161

The pesticidal particulate composition according to embodiment 160, wherein said basic substance is sodium bicarbonate.

Embodiment 162

The pesticidal particulate composition according to any one of embodiments 146 to 154, wherein said first active substance is an acidic substance and said second active substance is a basic substance.

Embodiment 163

The pesticidal composition according to embodiment 162 wherein said acidic substance is boric acid and said basic substance is $NaHCO_3$ which form $CO_2$ gas in the aqueous environment inside a pest body.

Embodiment 164

The pesticidal particulate composition according to embodiment 162 wherein said acidic substance is metaboric acid and said basic substance is $NaHCO_3$ which form $CO_2$ gas in the aqueous environment inside a pest body.

Embodiment 165

The pesticidal particulate composition according to any one of embodiments 146 to 164, wherein said second coating layer comprises at least one material selected from the group consisting of a foaming agent, a swelling agent, adhesive agent (e.g., a gum), anti-coalescence agent and any combination of the same.

Embodiment 166

The pesticidal particulate composition according to embodiment 165, wherein said adhesive agent is selected from the group consisting of xanthan gum, guar gum and any combination of the same.

Embodiment 167

The pesticidal particulate composition according to embodiment 166, wherein said foaming agent is carboxymethyl cellulose (CMC).

Embodiment 168

The pesticidal particulate composition according to embodiment 166, wherein said adhesive agent is xanthan gum or guar gum.

Embodiment 169

The pesticidal particulate composition according to any one of embodiments 146 to 166, wherein said second coating layer comprises carboxymethyl cellulose (CMC) and xanthan gum.

Embodiment 170

The pesticidal particulate composition according to embodiment 138, wherein said insect attractant is a flavoring agent, a pest/insect baiting agent or any combination of the same.

Embodiment 171

The pesticidal particulate composition according to embodiment 170, wherein said flavoring agent is sugar (e.g., a sugar produced from a sugar cane).

Embodiment 172

The pesticidal particulate composition according to embodiment 171, wherein said sugar is glucose.

Embodiment 173

The pesticidal particulate composition according to embodiment 170, wherein said baiting agent is a fragrance or a pheromone.

Embodiment 174

The pesticidal particulate composition according to embodiment 147, wherein said at least one insect attractant is selected from the group consisting of wood powder starch, dry bone powder, peanut powder, milk powder, vegetable powder, lactic acid, dead yeast powder, fish powder and any combination of the same.

Embodiment 175

The pesticidal particulate composition according to embodiment 148, wherein said at least one additive is selected from the group consisting of potato starch, sugar, salt, butyric acid and any combination of at least two of them.

Embodiment 176

The pesticidal particulate composition according to claim 148, wherein said additive is a combination of at least two of any of potato starch, powdered sugar, NaCl, KCl and butyric acid.

Embodiment 177

The pesticidal particulate composition according to claim 148, wherein said additive is a combination of at least two of any of potato starch, powdered sugar, NaCl, KCl and crystal methanol.

Embodiment 178

The pesticidal particulate composition according to any one of embodiment 146 to 177, wherein said first functional substance and said second functional substance are present in said composition at a ratio in accordance with the stoichiometry of the reaction between them upon contacting each other.

Embodiment 179

The pesticidal particulate composition according to any one of embodiment 146 to 178, wherein said first functional substance and said second functional substance are present in said composition at a an equimolar ratio (1:1).

Embodiment 180

The pesticidal particulate composition according to any one of embodiments 146 to 179 wherein said inert additive is selected from $CaSO_4$, CaO or any combination of the same.

Embodiment 181

The pesticidal particulate composition according to embodiment 180 wherein said inert additive is $CaSO_4$.

Embodiment 182

The pesticidal particulate composition according to embodiment 146 wherein said relaxant agent is KBr.

Embodiment 183

The pesticidal particulate composition of matter according to embodiment 41 or 42, wherein said composition comprises particles, each particle comprising a core of an admixture of said first active substance, said second active substance, said at least one inert additive and optionally at least one relaxant agent, wherein each said core is coated with said first coating layer;

wherein said first and second active substances form a gaseous product in the aqueous environment inside a pest body, wherein at least part of said gaseous product is in the form of gas bubbles;

wherein said first coating layer comprises at least one material which disintegrates at least in part in a substantially aqueous environment to thereby enable exposure of said first active substance and said second active substance to the aqueous environment inside a pest body;

wherein each of said particle is optionally further coated at least in part with said second coating layer wherein said second coating layer comprises a material which prevents coalescence of the gas bubbles formed at least in part by said first active substance and said second active substance.

Embodiment 184

A pesticidal particulate composition of matter comprising particles, the particles comprising a first active substance and a second active substance, wherein contact between the first and second active substances inside a pest body leads to:
(1) a reaction that generates at least one gaseous product, with or without heat generation; and/or
(2) an exothermic reaction generating heat;
wherein said at least one gaseous product and/or heat are capable of destroying the pest.

Embodiment 185

A pesticidal particulate composition of matter comprising particles, the particles comprising a first active substance, a second active substance and at least one inert additive, wherein the reaction between the first and second active substances upon contact inside a pest body (e.g., in the aqueous environment therein), generates heat, the heat being capable of destroying the pest.

Embodiment 186

A pesticidal particulate composition of matter comprising particles, the particles comprising a first active substance, a second active substance, at least one inert additive and optionally at least one relaxant agent, wherein the reaction between the first and second active substances upon contact inside a pest body (e.g., in the aqueous environment therein), generates heat, the heat being capable of destroying the pest.

Embodiment 187

A pesticidal particulate composition of matter comprising an individually coated first active substance and an individually coated second active substance, wherein the reaction between the first and second active substances upon contact with each other within a pest body generates heat, the heat being capable of destroying the pest.

Embodiment 188

A pesticidal particulate composition of matter comprising a mixture of particles of a first type and particles of a second type, each particle comprising a core of an active substance, individually coated at least in part with a first coating layer, wherein
the core of the first type particles comprises a first functional substance and the core of the second type particles comprises a second functional substance, the reaction between the first and second functional substances upon contact with each other (e.g., in aqueous environment inside a pest body) generating heat;

wherein the first coating layer comprises at least one material which prevents contact between the first and the second functional substance, which material disintegrates at least in part in a substantially aqueous environment to thereby enable contact between the first functional substance and the second functional substance, wherein the material in the first coating layer of the first type particles and in the first coating layer of the second type particles may be the same or different; and wherein optionally at least one of the first type particles and the second type particles further comprises a further coating layer which may be superimposed on the first coating layer.

Embodiment 189

A pesticidal particulate composition of matter comprising a first functional substance and a second functional substance, wherein the first and second functional substances are each individually coated at least in part with a first coating layer;

wherein the reaction between the first and second functional substances upon contact with each other (e.g., in an aqueous environment inside a pest body) generates heat;

wherein the first coating layer comprises at least one material which prevents contact between the first and the second functional substance, which material disintegrates at least in part in a substantially aqueous environment thereby enabling contact between the first functional substance and the second functional substance, wherein the material in the first coating layer of the first active substance and in the first coating layer of the second active substance may be the same or different;

wherein at least one of the first functional substance and the second functional substance is optionally further coated at least in part with same or different further coating layer; and wherein the first and second active substances are both comprised in a single particle.

Embodiment 190

A pesticidal particulate composition of matter comprising particles, each particle comprising a core of an admixture of a first functional substance, a second functional substance, at least one inert additive and optionally at least one relaxant agent, wherein each said core is coated at least in part with a first coating layer;

wherein the reaction between said first and second functional substances in the aqueous environment inside a pest body generates heat;

wherein the first coating layer comprises at least one material which disintegrates at least in part in a substantially aqueous environment to thereby enable exposure of the first functional substance and the second functional substance to the aqueous environment inside a pest body;

wherein each of said particle is optionally further coated at least in part with a further coating layer.

Embodiment 191

The pesticidal particulate composition according to any one of embodiments 184 to 190 wherein said first active substance is an acidic substance.

Embodiment 192

The pesticidal particulate composition according to embodiment 191, wherein said acidic substance is selected from the group consisting of boric acid, metaboric acid, formic acid, citric acid glycerin and any combination of the same.

Embodiment 193

The pesticidal particulate composition according to embodiment 192, wherein said acidic substance is boric acid ($H_3BO_3$).

Embodiment 194

The pesticidal particulate composition according to embodiment 192, wherein said acidic substance is metaboric acid ($HBO_2$).

Embodiment 195

The pesticidal particulate composition according to any one of embodiments 184 to 194, wherein said second active substance is a basic substance.

Embodiment 196

The pesticidal particulate composition according to embodiment 195, wherein said basic substance is selected from the group consisting of $NaHCO_3$, $CaCO_3$, $KMnO_4$ and any combination of the same.

Embodiment 197

The pesticidal particulate composition according to embodiment 196, wherein said basic substance is sodium bicarbonate.

Embodiment 198

The pesticidal particulate composition according to any one of embodiments 184 to 190, wherein said first active substance is an acidic substance and said second active substance is a basic substance.

Embodiment 199

The pesticidal particulate composition according to embodiment 198 wherein said acidic substance is boric acid and said basic substance is $NaHCO_3$.

Embodiment 200

The pesticidal particulate composition according to embodiment 198 wherein said acidic substance is metaboric acid and said basic substance is $NaHCO_3$.

Embodiment 201

The pesticidal particulate composition according to any one of embodiments 184 to 190, wherein said first active substance and said second active substance are present in said composition at a ratio in accordance with the stoichiometry of the reaction between them upon contacting each other (e.g., in a substantially aqueous environment).

Embodiment 202

The pesticidal particulate composition according to any of embodiments 184 to 200, wherein said first active substance and said second active substance are present in said composition at a an equimolar ratio (1:1).

Embodiment 203

The pesticidal particulate composition according to embodiments 184 or 187, wherein said first active substance and said second active substance are each individually coated at least in part with a first coating layer.

Embodiment 204

The pesticidal particulate composition according to any one of embodiments 184 to 186, wherein said particles are coated with a first coating layer.

Embodiment 205

The pesticidal particulate composition according to any one of embodiments 184 to 186, wherein the particles are each coated with a first coating layer.

Embodiment 206

The pesticidal particulate composition according to any one of embodiments 203 to 205, wherein said first coating layer comprises at least one material which prevents contact between said first active substance and said second active substance, which material disintegrates at least in part in a substantially aqueous environment thereby enabling contact between said first active substance and said second active substance.

Embodiment 207

The pesticidal particulate composition according to any one of embodiments 188 to 190 and 206, wherein said material is selected from the group consisting of proteins, carbohydrates, nutrients synthetic materials and any combination of the same.

Embodiment 208

The pesticidal particulate composition according to embodiment 207, wherein said protein is selected from the group consisting of dairy proteins, meat proteins, egg proteins, plant proteins and any combination of the same.

Embodiment 209

The pesticidal particulate composition according to embodiment 208, wherein said protein is whey protein.

Embodiment 210

The pesticidal particulate composition according to any one of embodiments 188 to 190 and 206, wherein said material is a hygroscopic material.

Embodiment 211

The pesticidal particulate composition according to embodiment 210, wherein said hygroscopic material is rice starch.

Embodiment 212

The pesticidal particulate composition according to any one of embodiments 188 to 190 and 206, wherein said first coating layer comprises at least one whey protein and rice starch.

Embodiment 213

The pesticidal particulate composition according to embodiment 203, wherein at least one of said first active substance and said second active substance is further coated at least in part with a same or different second coating layer.

Embodiment 214

The pesticidal particulate composition according to any one of embodiments 204 to 205, wherein said particles are further coated at least in part with a second coating layer.

Embodiment 215

The pesticidal particulate composition according to embodiment 213 or 214, wherein said second coating layer comprises at least one material selected from the group consisting of a foaming agent, a swelling agent, adhesive agent, anti-coalescence agent and any combination of the same.

Embodiment 216

The pesticidal particulate composition according to embodiment 215, wherein said adhesive agent is selected from the group consisting of xanthan gum, guar gum and any combination of the same.

Embodiment 217

The pesticidal particulate composition according to embodiment 215, wherein said foaming agent is carboxymethyl cellulose (CMC).

Embodiment 218

The pesticidal particulate composition according to embodiment 215, wherein said second coating layer comprises carboxymethyl cellulose (CMC) and xanthan gum.

Embodiment 219

The pesticidal particulate composition according to embodiment 213, wherein at least one of said first active substance and said second active substance is further coated at least in part with a third coating layer, wherein said third coating layer comprises at least one specific insect attractant.

Embodiment 220

The pesticidal particulate composition according to embodiment 214, wherein said particles are further coated at least in part with a third coating layer, wherein said third coating layer comprises at least one specific insect attractant.

Embodiment 221

The pesticidal particulate composition according to any one of embodiments 188 to 190, wherein said further coating layer comprises at least one specific insect attractant.

Embodiment 222

The pesticidal particulate composition according to any one of embodiments 219 to 221, wherein said specific insect attractant is a flavoring agent, a pest/insect baiting agent or any combination of the same.

Embodiment 223

The pesticidal particulate composition according to embodiment 222, wherein said flavoring agent is a sugar (e.g., a sugar prepared from a sugar cane).

Embodiment 224

The pesticidal particulate composition according to embodiment 223, wherein said sugar is glucose.

Embodiment 225

The pesticidal particulate composition according to embodiment 222, wherein said baiting agent is a fragrance or a pheromone.

Embodiment 226

The pesticidal particulate composition according to any one of embodiments 219 to 221, wherein said at least one insect attractant is selected from the group consisting of wood powder starch, dry bone powder, peanut powder, milk powder, vegetable powder, lactic acid, dead yeast powder, fish powder and any combination of the same.

Embodiment 227

The pesticidal particulate composition according to any one of the embodiments 184 to 226, wherein said composition further comprises at least one additive.

Embodiment 228

The pesticidal particulate composition according to embodiment 227, wherein said at least one additive is selected from the group consisting of potato starch, sugar, salt, butyric acid and any combination of at least two of them.

Embodiment 229

The pesticidal particulate composition according to embodiment 227, wherein said additive is a combination of at least two of any of potato starch, powdered sugar, NaCl, KCl and butyric acid.

Embodiment 230

The pesticidal particulate composition according to embodiment 227, wherein said additive is a combination of at least two of any of potato starch, powdered sugar, NaCl, KCl and crystal methanol.

Embodiment 231

The pesticidal particulate composition according to any one of embodiments 185, 186 and 190, wherein said inert additive is selected from the group consisting of $CaSO_4$, CaO and any combination of the same.

Embodiment 232

The pesticidal particulate composition according to embodiment 231, wherein said inert additive is a $CaSO_4$.

Embodiment 232

The pesticidal particulate composition according to embodiment 186 or 190, wherein said relaxant agent is KBr.

Embodiment 233

The pesticidal particulate composition according to any one of the preceding embodiments, wherein said composition is in the form of a powder.

Embodiment 234

A pesticidal preparation comprising a composition of matter as defined in any one of embodiments 1 to 233, optionally further comprising at least one of additives, excipients, diluents and carriers.

Embodiment 235

The preparation of embodiment 234, being an insecticidal preparation.

Embodiment 236

A method of controlling pests wherein said method comprising exposure of said pests to the pesticidal composition of matter according to any one of embodiments 1 to 233 or to the pesticidal preparation according to any one of embodiments 234 and 235.

Embodiment 237

The pesticidal composition according to any one of embodiments 1 to 233 as herein described.

Embodiment 238

The preparation according to any one of embodiments 234 and 235 as herein described.

Embodiment 239

A kit comprising:
a) particles of a first active substance;
b) particles of a second active substance;
c) means for mixing the constituents defined in a), b);
d) means for applying the mixed constituents of c) to a pest-infected environment; and
e) instructions for use.

Embodiment 240

A kit comprising:
a) a composition of matter according to the invention;
b) means for applying the composition of a) to a pest-infected environment; and
c) instructions for use.

In all embodiments in which particles are coated with more than one layer, for example, coated with two or three coating layers, the particles may be referred to as multilayered particles.

The invention claimed is:

1. A particulate composition of matter capable of destroying an insect upon entering the insect body, the particles of said composition comprising substances that function to destroy an insect upon entering the insect body, wherein said substances comprise a first active substance, a second active substance and a bubble stabilizing agent, said first active substance and said second active substances being chosen such that contact of said first active substance with said second active substance in an aqueous environment causes a reaction that generates at least one gaseous product, with or without heat generation, and said bubble stabilizing agent being chosen such that the bubbles of gaseous product formed in the aqueous environment are stabilized, and wherein each of the substances that function to destroy an insect upon entering the insect body are non-toxic.

2. The particulate composition according to claim 1, wherein said first active substance is an acidic substance and said second active substance is a basic substance.

3. The particulate composition according to claim 1, wherein said bubble stabilizing agent is selected from the group consisting of a foaming agent, a swelling agent, an adhesive agent, an anti-coalescence agent or any combination of at least two thereof.

4. The particulate composition according to claim 1, wherein said particles of the composition are each coated with a first coating layer.

5. The particulate composition according to claim 4, wherein said first coating layer comprises at least one material which disintegrates at least in part in a substantially aqueous environment, thereby enabling exposure of said first and second active substances to the aqueous environment in an insect body.

6. The particulate composition according to claim 4, wherein said bubble stabilizing agent is present in said first coating layer.

7. The particulate composition according to claim 4, wherein said particles are further coated at least in part with a second coating layer.

8. The particulate composition according to claim 7, wherein said bubble stabilizing agent is present in said second coating layer.

9. The particulate composition according to claim 7, wherein said bubble stabilizing agent is selected from the group consisting of a foaming agent, a swelling agent, an adhesive agent, an anti-coalescence agent and any combination of at least two thereof, and wherein said bubble stabilizing agent is present in the first or the second coating layer.

10. The particulate composition according to claim 7, wherein said particles are further coated at least in part with a third coating layer, wherein said third coating layer comprises at least one specific insect attractant.

11. The particulate composition according to claim 4, wherein said particles are further coated at least in part with a further coating layer wherein said further coating layer comprises at least one specific insect attractant.

12. The particulate composition according to claim 1, wherein each of said particles of the composition comprises both said first active substance and said second active substance.

13. The particulate composition according to claim 12, wherein at least one of said first active substance and said second active substance is coated with a coating layer comprising a material that prevents contact between said first and second active substances.

14. The particulate composition according to claim 1, wherein said first active substance and said second active substance are each comprised in different particles, wherein the particles in said composition are mixed at a ratio that provides a stoichiometric molar ratio between said first active substance and said second active substance in accordance with the stoichiometry of the said reaction between them upon contact.

15. A method of controlling insects, comprising exposing said insects to the particulate composition of matter according to claim 1.

* * * * *